United States Patent [19]
Hartle et al.

[11] Patent Number: 6,119,395
[45] Date of Patent: Sep. 19, 2000

[54] END SEALS FOR MANUFACTURING SEED

[75] Inventors: Jeffrey E. Hartle, Federal Way; William C. Carlson, Olympia; James A. Grob, Auburn, all of Wash.

[73] Assignee: Weyerhaeuser Company, Federal Way, Wash.

[21] Appl. No.: 09/016,827

[22] Filed: Jan. 30, 1998

Related U.S. Application Data

[60] Provisional application No. 60/035,122, Feb. 3, 1997.

[51] Int. Cl.$^7$ ............................................. A01C 1/06
[52] U.S. Cl. ................................. 47/57.6; 47/58.1
[58] Field of Search .................... 47/57.6, 58.1, 47/56

[56] References Cited

U.S. PATENT DOCUMENTS

| | | | |
|---|---|---|---|
| 2,309,702 | 2/1943 | Kirschenbaum | 47/56 |
| 2,502,809 | 4/1950 | Vogelsang | 47/58 |
| 3,098,320 | 7/1963 | Estokowski | 47/56 |
| 3,545,129 | 12/1970 | Schreiber et al. | 47/57.6 |
| 3,688,437 | 9/1972 | Hamrin | 47/57.6 |
| 3,734,987 | 5/1973 | Hamrin | 264/54 |
| 3,850,753 | 11/1974 | Chibata et al. | 195/109 |
| 4,166,006 | 8/1979 | Hertl et al. | 435/244 |

(List continued on next page.)

FOREIGN PATENT DOCUMENTS

| | | | |
|---|---|---|---|
| 1241552 | 9/1988 | Canada . | |
| 1250296 | 2/1989 | Canada . | |
| 0 107 141 | 5/1984 | European Pat. Off. . | |
| 0 300 730 A1 | 1/1989 | European Pat. Off. . | |
| 0 380 692 A1 | 8/1990 | European Pat. Off. . | |
| 61-040708 | 2/1986 | Japan . | |
| 62-275604 | 11/1987 | Japan . | |
| 63-133904 | 6/1988 | Japan . | |
| 63-152905 | 6/1988 | Japan . | |
| 2-46240 | 2/1990 | Japan . | |
| WO 91/01803 | 2/1991 | WIPO . | |
| WO 92/07457 | 5/1992 | WIPO | 47/57.6 |

OTHER PUBLICATIONS

Gray, Somatic Embryogenesis and Develpoment of . . . , Critical Reviews in Plant Science 10:33–61, Jan. 1, 1991.

Redenbaugh et al., "Encapsulation of Somatic Embryos in Synthetic Seed Coats," HortScience 21 (No. 3, Section 2): 819–820 (1986) (Abstract of presentation at XXII Int'l Hortic. Cong., Aug. 10–18, 1986, Davis. CA).

Redenbaugh et al., "Encapsulation of Somatic Embryos for Artificial Seed Production" (Abstract), In Vitro 20 (Part 2): 256–257 (1984).

Fujii et al., "Improving Plantlet Growth and Vigor from Alfalfa Artificial Seed" (Abstract), In Vitro 24 (No. 3, Part 2):70A (1989).

Fujii et al., "ABA Maturation and Starch Accumulation in Alfalfa Somatic Embryos" (Abstract), In Vitro 25 (No. 3, Part 2): 61A (1989).

Janick, "Production of Synthetic Seed via Desiccation and Encapsulation" (Abstract), In Vitro 24 (No. 3, Part 2):70A (1989).

Kamada et al., "New Methods for Somatic Embryo Induction and Their Use for Synthetic Seed Production" (Abstract), In Vitro 24 (No. 3, Part 2):71A (1988).

Bapat and Rao, "Sandalwood Plantlets from 'Synthetic Seeds,'" Plant Cell Reports 7:434–436 (1988).

Datta and Potrykus, "Artificial Seeds in Barley: Encapsulation of Microspore–Derived Embryos," Theor. Appl. Genet. 77:820–824 (1989).

(List continued on next page.)

Primary Examiner—Michael J. Carone
Assistant Examiner—Jeffrey L Gellner
Attorney, Agent, or Firm—Christensen O'Connor Johnson & Kindness PLLC

[57] ABSTRACT

The present invention provides manufactured seeds and related compositions and methods. The manufactured seeds comprise a unit of a totipotent plant tissue enclosed in a protective manufactured seed coat that includes an orifice sealed by a lid. The lid has a burst strength and architecture (e.g., a dome or nipple) similar to those of analogous structures in a natural botanic seed.

26 Claims, 7 Drawing Sheets

U.S. PATENT DOCUMENTS

| | | | |
|---|---|---|---|
| 4,252,827 | 2/1981 | Yokoyama et al. | 424/366 |
| 4,465,017 | 8/1984 | Simmons | 118/418 |
| 4,562,663 | 1/1986 | Redenbaugh | 47/58 |
| 4,583,320 | 4/1986 | Redenbaugh | 47/57.6 |
| 4,615,141 | 10/1986 | Janick et al. | 47/57.6 |
| 4,665,648 | 5/1987 | Branco et al. | 47/57.6 |
| 4,715,143 | 12/1987 | Redenbaugh et al. | 47/57.6 |
| 4,769,945 | 9/1988 | Motoyama et al. | 47/57.6 |
| 4,777,762 | 10/1988 | Redenbaugh et al. | 47/57.6 |
| 4,779,376 | 10/1988 | Redenbaugh | 47/57.6 |
| 4,780,987 | 11/1988 | Nelson et al. | 47/57.6 |
| 4,802,305 | 2/1989 | Kojimoto et al. | 47/57.6 |
| 4,806,357 | 2/1989 | Garrett et al. | 427/4 |
| 4,808,430 | 2/1989 | Kouno | 427/4 |
| 4,866,096 | 9/1989 | Schweighardt | 514/756 |
| 4,879,839 | 11/1989 | Gago et al. | 47/57.6 |
| 5,010,685 | 4/1991 | Sakamoto et al. | |
| 5,044,116 | 9/1991 | Gago et al. | |
| 5,250,082 | 10/1993 | Teng et al. | |
| 5,284,765 | 2/1994 | Bryan et al. | |
| 5,451,241 | 9/1995 | Carlson | 47/57.6 |
| 5,564,224 | 10/1996 | Carlson | 47/57.6 |
| 5,701,699 | 12/1997 | Carlson | 47/57.6 |
| 5,732,505 | 3/1998 | Carlson | 47/57.6 |

OTHER PUBLICATIONS

Fujii et al., "Artificial Seeds for Plant Propagation," *Trends in Bio/Technol.* 5:335–339 (1987).

Gupta and Durzan, "Biotechnology of Somatic Polyembryogenesis and Plantlet Regeneration in Loblolly Pine," *Bio/Technol.* 5:147–151 (1987).

Ibarbia, "Synthetic Seed: Is It the Future," *Western Grower and Shipper* 59:12 (1988).

Kim and Janick, "ABA and Polyox–Encapsulation or High Humidity Increases Survival of Desiccated Somatic Embryos of Celery," *HortScience* 24:674–676 (1989).

Kitto and Janick, "Production of Synthetic Seeds by Encapsulating Asexual Embryos of Carrot," *J. Amer. Soc. Hort. Sci.* 100:277–282 (1985).

Kitto and Janick, "A Citrus Embryo Assay to Screen Water–Soluble Resins as Synthetic Seed Coats," *HortScience* 20:98–100 (1985).

Redenbaugh et al., Encapsulated Plant Embryos, in *Biotechnology in Agriculture*, pp. 225–248 (1988).

Redenbaugh et al., "Somatic Seeds: Encapsulation of Asexual Plant Embryos," *Bio/Technol.* 4:797–801 (1986).

Redenbaugh et al., "Encapsulation of Somatic Embryos in Synthetic Seed Coats," *HortScience* 22:803–809 (1987).

Redenbaugh et al., "Scale–Up: Artificial Seeds," in Green et al. (eds.), *Plant Tissue and Cell Culture*, pp. 473–493, Alan R. Liss, NY (1987).

Rogers, "Synthetic–Seed Technology," *Newsweek*, Nov. 28, 1983.

Stuart and Redenbaugh, "Use of Somatic Embryogenesis for the Regeneration of Plants," in LeBaron et al. (eds.), *Biotechnology in Agricultural Chemistry*, Ch. 6, pp. 87–96, American Chemical Society, Washington, D.C. (1987).

Teasdale and Buxton, "Culture of *Pinus Radiata* Embryos with Reference to Artificial Seed Production," *New Zealand J. For. Sci.* 16:387–391 (1986).

Adlercreutz and Mattiasson, "Oxygen Supply to Immobilized Cells: 1. Oxygen Production by Immobilized *Chlorella pyrenoidosa*," *Enzyme Microbial Technol.* 4:332–336 (1982).

Adlercreutz and Mattiasson, "Oxygen Supply to Immobilized Biocatalysts. A Model Study," *Acta Chem. Scand.* B36:651–653 (1982).

Adlercreutz and Mattiasson, "Oxygen Supply to Immobilized Cells. 3. Oxygen Supply by Hemoglobin or Emulsions of Perfluorochemicals," *Eur. J. Appl. Microbiol. & Biotechnol.* 16:165–170 (1982).

Mattiasson and Adlercreutz, "Use of Perfluorochemicals for Oxygen Supply to Immobilized Cells," *Ann. N.Y. Acad. Sci.* 413:545–547 (1984).

Damiano and Wang, "Novel Use of a Perfluorocarbon for Supplying Oxygen to Aerobic Submerged Cultures," *Biotechnol. Letters* 7:81–86 (1985).

Chandler et al., "Effects of Emulsified Perfluorochemicals on Growth and Ultrastructure of Microbial Cells in Culture," *Biotechnol. Letters* 9:195–200 (1987).

King et al., "Perfluorochemicals and Cell Culture," *Biotechnol.* 7:1037–1042 (1989).

Clark et al., "The Physiology of Synthetic Blood," *J. Thorac. & Cardiovasc. Surg.* 60:757–773 (1970).

Fujita et al., "Fluorocarbon Emulsion as a Candidate for Artificial Blood," *Europ. Surg. Res.* 3:436–453 (1971).

Geyer, "'Bloodless' Rats Through the Use of Artificial Blood Substitutes," *Fed. Proceed.* 34:1499–1505 (1975).

Clark et al., "Emulsions of Perfluoronated Solvents for Intravascular Gas Transport," *Fed. Proceed.* 34:1468–1477 (1975).

Riess and Le Blanc, "Perfluoro Compounds as Blood Substitutes," *Angew. Chem. Int. Ed. Engl.* 17:621–634 (1978).

Davis et al., "Novel Compositions of Emulsified Perfluorocarbons for Biological Applications," *Brit. J. Pharmacol.* 89:665P (1986).

"FLUORINERT™ Electronic Liquids" brochure, 3M Industrial Chemical Products Division, St. Paul, Minnesota (1989).

"'FLUORINERT™ Electronic Liquids' for Direct Contact Dielectric Cooling" brochure, Chemical Products Division, St. Paul, Minnesota (1989).

Bapat et al., "In Vivo Growth of Encapsulated Axillary Buds of Mulberry, (*Morus indica* L.)," *Plant Cell, Tissue and Organ Culture* 20:69–70 (1990).

Li, "Somatic Embryogenesis and Synthetic Seed Technology Using Carrot as a Model System," in *Synseeds: Applications of Synthetic Seeds to Crop Improvement*, Redenbaugh, Ed., CRC Press, Florida (1993), chap. 16.

Sanada et al., "Celery and Lettuce," in *Synseeds: Applications of Synthetic Seeds to Corp Improvement*, Redenbaugh, Ed., CRC Press, Florida (1993), chap. 17.

Bapat, "Studies on Synthetic Seeds of Sandalwood (*Santalum album* L.) and Mulberry (*Morus indica* L.)," in *Synseeds: Applications of Synthetic Seeds to Crop Improvement*, Redenbaugh, Ed., CRC Press, Florida (1993), chap. 21.

Senaratna, "Artificial Seeds," *Biotech. Adv.* 10:379–392 (1992).

Redenbaugh et al., "III.3 Artificial Seeds—Encapsulated Somatic Embryos," *Biotech. in Agr. & For.* 17:395–416 (1991).

Buchenauer, "Mode of Action and Selectivity of Fungicides Which Interfere with Ergosterol Biosynthesis," Proceedings 1977 British Crop Protection Conference—Pests and Diseases (1977).

Dumet et al., "Cryopreservation of Oil Palm (*Elaeis guincesis* Jacq.) Somatic Embryos Involving a Desiccation Step," *Plant Cell Rep.* 12:352–355 (1993).

Paulet et al., "Cryopreservation of Apices of in vitro Plantlets of Sugarcane (Saccharum sp. Hybrids) Using Encapsulation/Dehydration," *Plant Cell Rep.* 12:525–529 (1993).

Tessereau et al., "Cryopreservation of Somatic Embryos: A Tool for Germplasm Storage and Commercial Delivery of Selected Plants," *Ann. Bot.* 74:547–555 (1994).

Ebert et al., "Inheritance of Pericarp Types, Sterility, and Dwarfness in Several Safflower Crosses," *Crop Sci.* 6:579–582 (1966).

Gray et al., "Somatic Embryogenesis and Development of Synthetic Seed Technology," *Crit. Rev. Plant Sci.* 10:33–61 (1991).

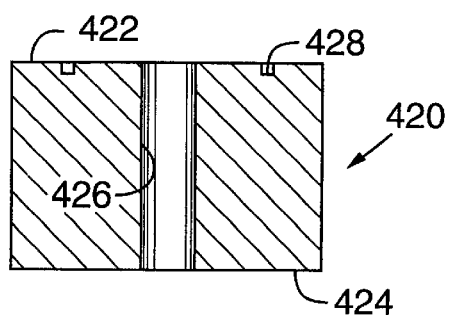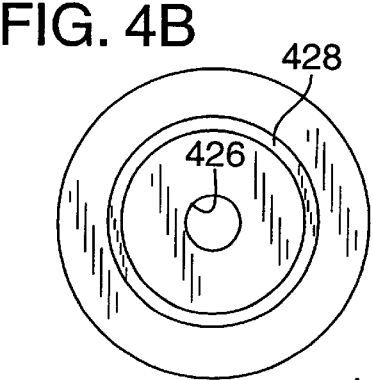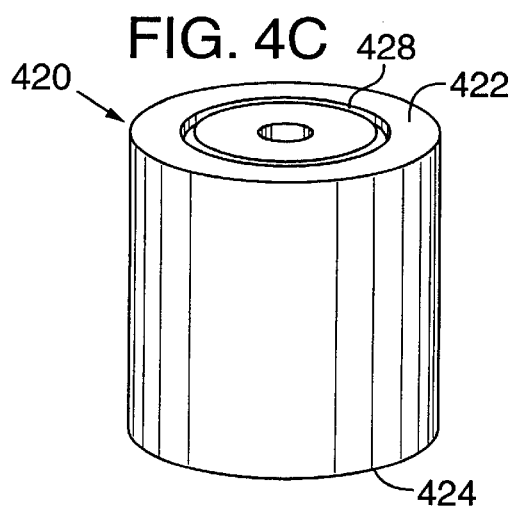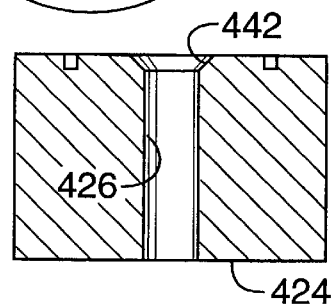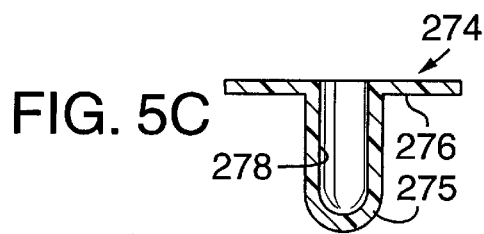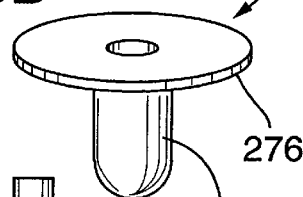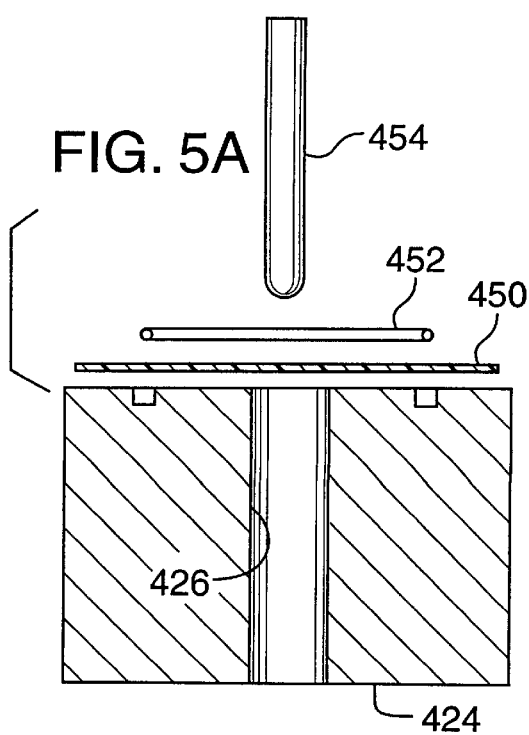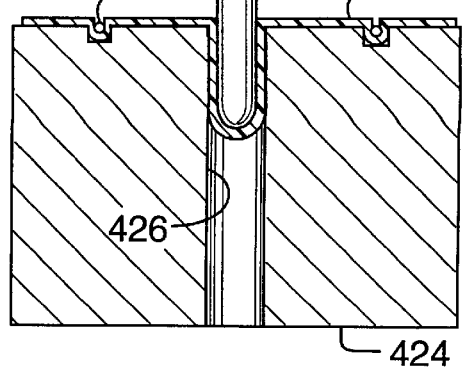

END SEALS FOR MANUFACTURING SEED

CROSS REFERENCE TO RELATED APPLICATION

This application claims the benefit of U.S. Provisional Application Ser. No. 60/035,122, filed Feb. 3, 1997, which is incorporated herein by reference.

FIELD OF THE INVENTION

This invention relates to manufactured seed, each containing a unit of totipotent plant tissue, that can be sown like natural seed and produce viable germinants.

BACKGROUND OF THE INVENTION

Modern agriculture, including silviculture, often requires the planting of large numbers of substantially identical plants genetically tailored to grow optimally in a particular locale or to possess certain other desirable traits. Production of new plants by sexual reproduction, which yields botanic seeds, can be time- and labor-intensive and is often subject to genetic recombinational events resulting in variable traits in the progeny. Further, inbred strains such as those used to perform such crosses often lack vigor, resulting in low seed productivity.

In vitro culture of somatic or zygotic plant embryos can be used to produce large numbers of genetically identical embryos that have the capacity to develop into normal plants. However, the resulting embryos lack the protective and nutritive structures found in natural botanic seeds that shelter the plant embryo inside the seed from the harsh soil environment and nurture the embryo during the critical stages of sowing and germination. As a result, the embryos must usually be further cultured in vitro until they reach a "seedling" state characterized by the ability to photosynthesize, resist desiccation, produce roots able to penetrate soil, and fend off soil microorganisms. As used herein, the terms "Artificial" or "manufactured" seeds refer to seeds in which individual plant somatic or zygotic embryos are encapsulated in a hydrated gel. In the most advanced designs, the manufactured seed includes various protective and nutritive features that more closely mimic analogous structures of natural botanic seed.

There is a need for an improved manufactured seed that more closely mimics the function of natural, botanic seed by protecting the embryo against mechanical damage, desiccation, and attack by pathogens, herbivores, and pests, and promoting a high rate of germination. The present invention meets these and other needs.

SUMMARY OF THE INVENTION

The present invention provides manufactured seeds comprising a plant embryo or other unit of totipotent plant tissue. The totipotent plant tissue is enclosed and thus protected by a manufactured seed coat that has an orifice covered by a secondary end seal, or lid. The lid has a protruding portion that the totipotent plant tissue preferentially enters and contacts upon germination, facilitating the emergence of a plant germinant from the manufactured seed by dislodging or penetrating the lid. For this reason, the radicle of the totipotent plant tissue is oriented toward the protruding portion of the lid. The burst strength and cross-sectional diameter of the nipple is selected to optimize the speed of germination and germinant normalcy for totipotent plant tissue of a given plant species.

According to another embodiment of the invention, a manufactured seed is provided that includes a totipotent plant tissue enclosed by a manufactured seed coat that has an orifice covered by a lid that includes a protruding portion, e.g., a nipple-, dome- or finger-like structure that protrudes outwardly from the manufactured seed. Upon germination, the totipotent plant tissue preferentially enters and contacts the protruding portion of the lid and dislodges or penetrates the lid. Preferably, the lid (at least the protruding portion thereof) is penetrable by the totipotent plant tissue upon germination.

According to another embodiment of the invention, such a lid includes a wax or polymer film, for example Parafilm™. Preferably, the lid is made from a material that is water-impermeable and gas-permeable.

The protruding portion or "nipple" may be produced by any conventional method. According to one embodiment the lid is produced by pre-stretching a wax or polymer film such as Parafilm™ with a probe, resulting in a nipple that includes a generally cylindrical portion having a diameter similar to that of the probe. Preferably, the diameter of the probe is selected so as to produce a nipple having a cross-sectional diameter selected to provide significantly better germination than a flat lid of the same material. For Douglas-fir and loblolly pine, for example, it is preferable that the probe (and thus the resulting nipple) has a diameter between about 1.52 mm and about 3.35 mm.

According to another embodiment of the invention, the manufactured seed coat is water-impermeable until the totipotent plant tissue penetrates or dislodges the lid.

The totipotent plant tissue is preferably disposed relative to, and preferably surrounded by or in contact with, a hydrated gel so as to allow the transfer of liquid, dissolved solutes, and gases from the gel to the plant tissue. The gel thus serves as an "synthetic gametophyte" for the plant tissue in a manner analogous to the gametophyte portion of a natural botanic seed, i.e., the endosperm or other seed nutritive tissue, depending upon the species from which the totipotent plant tissue originates. Therefore, according to another embodiment of the invention, the manufactured seed includes a nonphytotoxic hydrated gel (e.g., an oxygenated gel) disposed within the manufactured seed coat so as to permit liquid transfer from the gel to the totipotent plant tissue.

According to another embodiment of the invention, the manufactured seed coat includes a material selected from the group consisting of a cellulosic material, glass, plastic, a cured polymeric resin, paraffin, wax, varnish, and combinations thereof.

According to another embodiment of the invention, methods of making manufactured seeds are provided that include the steps of: providing a manufactured seed coat that includes an orifice, inserting a totipotent plant tissue into the manufactured seed coat through the orifice, and covering the orifice with a lid that comprises a protruding portion such that, upon germination of the totipotent plant tissue, the totipotent plant tissue preferentially enters and contacts the protruding portion and dislodges or penetrates the lid.

According to another embodiment of the invention, such methods include the steps of: pre-stretching a wax or polymer film (for example, pre-stretching Parafilm™ with a probe) to produce the lid; and inserting the totipotent plant tissue into the manufactured seed coat such that the radicle is oriented toward the orifice. If the manufactured seed coat includes a nonphytotoxic hydrated gel, such methods include the step of disposing the totipotent plant tissue within the manufactured seed coat so as to permit liquid transfer from the gel to the totipotent plant tissue.

According to another embodiment of the invention, methods are provided for germinating a totipotent plant tissue that include the step of incubating a manufactured seed as described above under conditions suitable for germination of the totipotent plant tissue.

As discussed more fully below, manufactured seed according to the present invention may also include some provision for a restraint enclosing at least the shoot end of the totipotent plant tissue. These and other features result in manufactured seeds characterized by a high percent of germination of plant embryos therefrom.

The foregoing objects and other features and advantages of the present invention will be more fully understood as the detailed description thereof proceeds, particularly when considered together with the accompanying drawings.

BRIEF DESCRIPTION OF THE DRAWINGS

FIGS. 4A is a cross-sectional view of a standard (straight) mold for pre-stretching lids.

FIG. 4B is a top view of the standard mold of FIG. 4A.

FIG. 4C is a plan view of the standard mold of FIG. 4A.

FIG. 4D shows a cross-sectional view of a bevelled mold for pre-stretching lids.

FIGS. 5A–B show the process for pre-stretching Parafilm™ to produce a lid.

FIG. 5C shows a cross-sectional view of a pre-stretched lid.

FIG. 5D shows a plan view of the lid of FIG. 5C.

DETAILED DESCRIPTION OF THE PREFERRED EMBODIMENTS

Figure 1A:
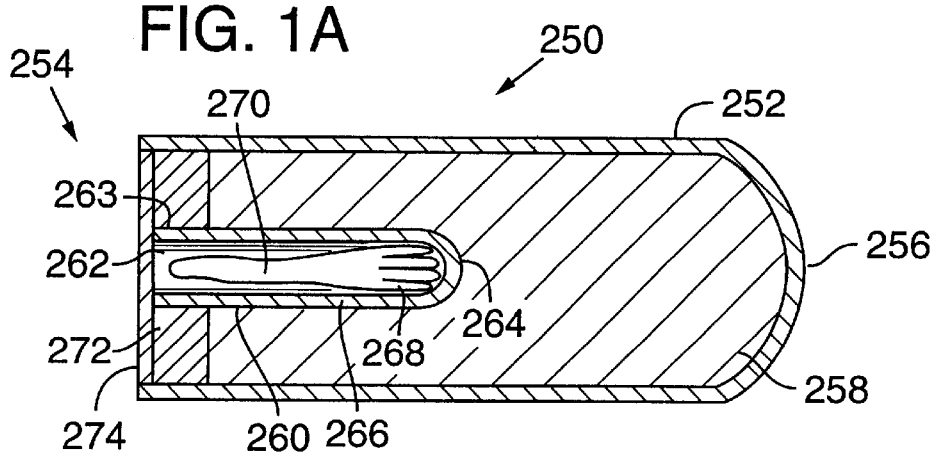
FIG. 1A is a sectional view of a manufactured seed with a flat lid.

The detailed description that follows is based on manufactured seed designs described, for example, in U.S. Pat. Nos. 5,236,469 and 5,701,699 (both incorporated herein by reference), with improved secondary end seals, or lids, as discussed in detail below. However, lids according to the present invention can be used in conjunction with any manufactured seed design, including, but not limited to, those discussed in U.S. Pat. Nos. 4,769,945 and 5,382,269 and Dupuis et al., Bio/Technology 12:385–389, 1994 (all incorporated herein by reference), in which a lid as described herein could be used to cover an opening in a capsule, vessel, or other structure enclosing a unit of totipotent plant tissue and a hydrated gel, thereby facilitating emergence of the plant tissue from its enclosure by penetrating or dislodging the lid.

Totipotent Plant Tissue

A manufactured seed, according to one aspect of the present invention, comprises a unit of totipotent plant tissue. As used herein, "totipotent" refers to a capacity to row and develop into a normal plant. Totipotent plant tissue has both the complete genetic information of a plant and the ready capacity to develop into a complete plant if cultured under favorable conditions. As is generally known in the art, totipotent plant tissue is obtainable from any of several areas of a plant, such as meristematic tissue and plant embryonic tissue.

Meristematic tissue is comprised of undifferentiated plant cells that divide to yield other meristematic cells, as well as differentiated cells that elongate and further specialize to form structural tissues and organs of the plant. Meristematic tissue is located, for example, at the extreme tips of growing shoots or roots, in buds, and in the cambium layer of woody plants.

Plant embryonic tissue can be found (in the form of a "zygotic" embryo) inside a botanic seed of the plant produced by sexual reproduction. Also, plant "somatic" embryos can be produced by culturing totipotent plant tissue such as meristematic tissue by standard methods under laboratory conditions in which the cells comprising the tissue are separated from one another and urged to develop into minute complete embryos. Alternatively, a process termed "cleavage polyembryogeny" known in the art can be induced during natural embryo development in seed.

As used herein, a "unit" of totipotent plant tissue is a mass of such tissue that can be individually handled and that can develop into a germinant and ultimately a plant under favorable conditions.

For use in preferred embodiments of manufactured seeds according to the present invention, the unit of totipotent plant tissue preferably is developed sufficiently to have a shoot end and a radicle end. In certain species of plants, the shoot end includes one or more cotyledons in some stage of development. For example, such totipotent plant tissue of gymnosperms usually has multiple cotyledons situated on or near the shoot apex. This is also the case with many dicotyledonous plants. In other types of plants, the cotyledon(s) are situated in locations other than the shoot end.

Manufactured seed according to the present invention can include a totipotent plant tissue from any plant species (dicotyledonous, monocotyledonous, gymnosperm, etc.).

Manufactured Seed Coat

The manufactured seed can include a manufactured seed coat that, like a natural seed coat, protects the totipotent plant tissue and other internal structures of the manufactured seed from mechanical damage, desiccation, from attack by microbes, fungi, insects, nematodes, birds, and other pathogens, herbivores, and pests, among other functions.

The manufactured seed coat can be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are substantially non-toxic and preferably provide a degree of rigidity. It is preferable that the seed coat be biodegradable, although it is also preferable that the seed coat remain intact until after emergence of the germinating totipotent plant tissue. It is also preferable that, until after emergence, the seed coat be resistant to penetration by microbial or other plant pathogens.

The manufactured seed coat includes a "shell" that has an opening or orifice that is covered or otherwise occluded by a lid and that contains a unit of totipotent plant tissue. Alternatively, in place of an orifice, the shell can include a region that is thin or weakened relative to other regions of the shell. The covered orifice or thinner or weakened portion has a lower burst strength than the rest of the shell. Thus, a germinating embryo preferentially emerges from the manufactured seed coat by penetrating through the opening or thinner or weaker portion of the shell. The shell is preferably sufficiently rigid to provide mechanical protection to the embryo, e.g., during sowing, and is substantially impermeable to gases, water, and soil microbes. It is preferable that the radicle of the totipotent plant tissue be oriented toward the opening or weaker area of the shell to facilitate protrusive growth of the primary root of the germinating totipotent plant tissue from the manufactured seed.

If the seed coat lacks an opening or weakened or thin section, the seed coat must not prevent the totipotent plant tissue germinating from within from growing out of the manufactured seed without fatal or debilitating injury to the tissue. To this end, polymeric materials having a high dry strength and low wet strength can be used. The seed coat can also be so constructed that it breaks apart easily upon application of an outwardly protrusive force from inside the manufactured seed but is relatively resistant to compressive forces applied to the outside of the seed coat, e.g., a self-breaking capsule (see, e.g., Japanese Patent Application No. JP 59102308 [Masuda and Sakamoto, published 1993] and Redenbaugh, "Introduction," In: Redenbaugh (ed.), *Synseeds: Application of Synthetic Seeds to Crop Improvement*, Chapter 1, CRC Press, Boca Raton, Fla., 1993). However, such an embodiment is less preferred, since the totipotent plant tissue can readily desiccate and is exposed to attack by pathogens, pests, and herbivores when the seed coat breaks.

The manufactured seed coat can have two or more layers, each having the same or a different composition. For example, the innermost layer can comprise a relatively compliant and water-impermeable cellulosic material and the outer layer can comprise a polymeric material having a high dry strength and a low wet strength. Alternatively, the inner layer can comprise a rigid shape such as an open-ended cylinder, where at least a portion of the open end(s) is covered with an outer-layer material having a high dry strength and a low wet strength.

Further alternatively, the seed coat can comprise a relatively compliant cellulosic or analogous material, shaped to at least partially conform to the shape of the mass of hydrated gel to be disposed therein, and having at least one tapered end. The tapered end terminates with an orifice which is preferably covered with a lid.

Additives such as plant nutrients, antibiotics, and plant-growth regulators can be added to the manufactured seed coat, for example, by incorporation into the material forming one or more of the layers of the seed coat or by coating or otherwise treating the layer(s) with the additive by conventional means.

Although it is preferred that a manufactured seed according to the present invention have a hydrated gel disposed within the manufactured seed coat, the gel can be absent. If the gel is absent, it is preferred that the manufactured seed coat be selected to prevent mechanical damage to the totipotent plant tissue, e.g., be rigid and physically support the plant tissue. If the gel is absent, it is also preferred that the manufactured seed coat include a lid to prevent desiccation and penetration by pathogens and pests while allowing gas exchange.

Secondary End Seal or Lid

Our working model is that a natural seed, which includes an embryo and a megagametophyte-seed coat complex, has evolved a structure and a pattern and rate of germination that results in successful germination under variable environmental conditions. Therefore, the various parts of a manufactured seed preferably function as much as possible like the analogous structure of a natural botanic seed.

One of the first occurrences during natural seed germination is the stretching of the nucellar membrane. As the radical grows, it presses against the nucellar membrane (nucellus), which is stretched and then punctured at the apex. An annulus remains after the nucellar cap breaks away from the megagametophyte.

As a root moves through the soil, it squeezes into the gap between soil particles and exerts force perpendicular to the particles, i.e., normal to the curvature of the root tip, thereby separating the particles. We hypothesized that the root applies pressure to the apex of the nucellar cap in the same way.

A secondary end seal, or lid, is disposed across and preferably completely covers and seals an opening or orifice in the manufactured seed coat. The lid functions as a synthetic analog of the nucellar membrane or analogous structures in a seed and preferably is similar in structure and function to such natural structures. The lid is penetrable or capable of being dislodged by the germinating totipotent plant tissue (particularly the radicle thereof) to permit the tissue to emerge from the manufactured seed, yet provides sufficient physical restraint to retain the plant tissue within the protective seed coat during handling of the manufactured seed.

It is preferable that the lid be substantially impermeable to liquid water ("water-impermeable"), gas-permeable, and be able to substantially retard pathogen entry. In addition, it is preferable that the lid reduce water loss and desiccation of the totipotent plant tissue.

Preferably, the lid comprises a wax or polymer film or membrane, preferably a thin, gas-permeable, water-impermeable membrane. A preferred end-seal material is a Parafilm® (American National Can, Greenwich, Conn.). Alternative materials include, but are not limited to, any of various thin polymeric films, e.g., stretchable films such as Duraseal™ (Sigma, St. Louis, Mo.), Cellulon™, polymer films used for packaging fresh fruits and vegetables (including films used for modified atmosphere packaging), wax-impregnated cellulosic tissue (e.g., Kimwipe™, Kimberly-Clark, Roswell, Ga.), or other conventional materials. Such secondary end-seal materials may be provided in combination with other materials, for example multi-layer composite materials having one or more wax and/or polymeric film plies, provided that at least a portion of the lid can be penetrated or dislodged by the totipotent plant tissue upon germination. A lid made from Parafilm™, for example, is water-impermeable when properly sealed and permeable to oxygen and other gases. Water vapor loss from manufactured seed with unstretched or pre-stretched Parafilm™ lids is very slow, preventing desiccation of the hydrated gel and plant tissue.

It is preferred that at least a portion of a lid for manufactured seed has a burst strength that is less than or equal to the force generated by germinating totipotent plant tissue from a given plant species, thus permitting the totipotent plant tissue (particularly the elongating radicle) to penetrate through the lid upon germination. Preferably, the burst strength of the lid (or at least a portion thereof, such as the protruding portion, or nipple, described below) is similar to that of the nucellar membrane or analogous structures in a natural botanic seed of the plant species. For a given species, an optimal burst strength can be estimated by determining the force necessary for an embryo to penetrate enclosing tissues of a natural seed of the species during germination.

The force required for an embryo to penetrate a natural seed can be determined by using a penetrometer or Instron™ machine (see, e.g., Welbaum et al., *J. Exper. Bot.* 46:391–400, 1995). When determining this force, it should be noted that there may be enzymatic weakening of the enclosing tissues in natural seed. Endosperm softening appears to be necessary for germination of various types of natural seed (Welbaum and Bradford, *Plant Physiol.* 92:1046–1052, 1990; Miguel and Sanchez, *J. Exper. Bot.* 43:969–974, 1992). The nucellar cap (nucellus) of a natural seed is degraded by enzymes prior to embryo germination (Welbaum et al., *J. Exper. Bot.* 46:391–400, 1995). Such enzymatic degradation should be accounted for to accurately estimate the force required for the plant tissue to emerge from enclosing tissues. The desired burst strength can also be determined (or further defined) empirically by determining the germination rate of manufactured seed having lids of different burst strengths.

A lid material having an appropriate burst strength (e.g., at the lower end of the force range for a given plant species) can then be selected, or a desirable material can be pre-stretched or otherwise weakened by conventional means (e.g., heating or chemical weakening by solvent application) so that at least a portion of the lid has the desired burst strength. Pre-stretching or otherwise weakening at least a portion of the lid reduces the force necessary for radicle penetration of the lid, allowing one to use materials that would otherwise be difficult or impossible for totipotent plant tissue to penetrate. Wax or polymer films, for example, can be pre-stretched in one or both linear dimensions to produce lids, by pressing a probe with a blunt end into the film to create a stretched region, or by other conventional means.

Preferably, at least a portion of the lid protrudes outwardly such that upon germination, the elongating radicle (or other elongating tissue) preferentially enters and contacts the protruding portion and eventually either dislodges the lid or penetrates the protruding portion thereof. As discussed in detail below, pre-stretching Parafilm™ with a substantially rigid generally cylindrical probe with a blunt (e.g., rounded) end produces a protruding portion shaped like a dome, nipple, or finger. The protruding portion is therefore analogous to the bulge observed in the nucellar cap of a Douglas-fir gametophyte, for example, as it stretches upon germination prior to the emergence of the radicle. However, the protruding portion of the lid can be produced by any conventional method of shaping materials such as wax or polymer films, such as molding, embossing, etc., and need not be of any particular shape.

The protruding portion of the lid causes the elongating radicle to preferentially enter and contact an area having an optimal burst strength. In at least some embodiments (e.g., with a pre-stretched Parafilm™ nipple), the lid curves around the root tip so that maximal force can be applied by the root. Moreover, the protruding portion allows the germinating embryo to become slightly larger before the radicle penetrates the lid (a) may result in tighter cotyledon contact with the surface of the cotyledon restraint; (b) facilitates better nutrient uptake (by equal and opposite reaction to the force of the root tip on the lid) for a longer period of time; (c) results in a longer radicle prior to bursting of the lid; (d) increases the dependency of the germinant on water in the soil rather than water in the seed; and (e) reduces pathogen entry into the seed until the germinant is larger. Parafilm™ lids that are pre-stretched to produce a nipple are associated with earlier germination (days to 50% germination) and higher normalcy rates. Even for materials that have a desirable burst strength without pre-stretching or weakening, it is nonetheless desirable to form or mold the lid to provide such a protruding portion to provide some or all of these advantages.

The diameter (and depth) of the nipple in a pre-stretched lid can affect the germination rate and normalcy of plant germinants. For Douglas-fir and loblolly pine, for example, lids produced from Parafilm™ using probes between about 1.50 mm and less than about 3.35 mm, and especially between about 2.00 mm and about 2.90 mm, gave the best results. For other plant species, the optimal nipple size (diameter and depth) can be determined empirically as described in the Examples below. For example, preferably after determining the burst strength of the nucellar membrane or analogous structure of natural botanic seeds of a plant species, nipples can be produced to have the desired burst strength by probes having varying diameters.

An antibiotic can be placed under the lid to prevent invasion by a bacterial or fungal pathogen or other pest. If the antibiotic is a beneficial microorganism, the microorganism can "inoculate" the primary root as it penetrates the lid during germination.

Hydrated Gels

A "gel" is a substance that is prepared as an aqueous colloidal solution and that will, or can be caused to, form a semisolid material. (As used herein, "hydrated" denotes the presence of free water interspersed throughout the matrix of gel molecules.) Conversion of a liquid gel solution into a semisolid material is termed herein "curing" or "setting" of the hydrated gel. In manufactured seeds according to the present invention, the hydrated gel, along with any other substances included therein, can serve as an "artificial gametophyte" for the totipotent plant tissue.

As can be ascertained from the foregoing, "hydrated" denotes water-containing. Hydrated gels are prepared by first dissolving in water (where water serves as the solvent, or "continuous phase") a hydrophilic polymeric substance (serving as the solute, or "disperse phase") that, upon curing, combines with the continuous phase to form the semisolid material. In other words, the water becomes homogeneously associated with the solute molecules without experiencing any substantial separation of the continuous phase from the disperse phase. However, water molecules can be freely withdrawn from a cured hydrated gel, such as by evaporation or imbibition by germinating plant tissue. When cured, a hydrated gel has the familiar characteristic of a compliant solid, like a mass of gelatin, where the compliance becomes progressively less and the gel becomes more "solid" to the touch as the relative amount of water in the gel is decreased.

In addition to being water-soluble, suitable gel solutes are not cytotoxic and substantially non-phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting some other vital process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of phytotoxicity. Also, it is important to be able to add, as required, other substances such as plant nutrients, antibiotics, plant growth regulators, or emulsified materials to a gel without substantially interfering with gelling ability.

Hydrated gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Certain gels are termed "reversible" because reheating the cured hydrated gel will re-form the gel solution. Other gels typically require a "complexing" agent serving to chemically cure the gel by crosslinking gel solute molecules. For example, sodium alginate is cured by adding calcium nitrate ($Ca(NO_3)_2$) or salts of other divalent ions such as, but not limited to, calcium, barium, lead, copper, strontium, cadmium, zinc, nickel, cobalt, magnesium, and iron to the gel solution. Many of the gel solutes requiring complexing agents are termed "irreversible" because reheating will not re-establish the gel solution.

The concentration of gel solute required to prepare a satisfactory hydrated gel varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. (As used herein, the "% w/v" concentration unit is equivalent to grams of solute per 100 ml of solvent.) Gel concentrations up to about 24% w/v have been successfully employed for other gels. In general, gels cured by complexing require less gel solute to form a satisfactory gel than "reversible" gels.

It is preferable to provide the totipotent plant tissue with any of various additives, e.g., plant nutrients and other beneficial substances such as vitamins and a source of carbon and energy (herein collectively termed generally "nutrients"), antibiotics, or plant growth regulators. See, e.g., the "adjuvants" listed in U.S. Pat. No. 4,779,376 (incorporated herein by reference). The additives can be provided by dissolving the gel solute in a solution of the additives or adding a volume of a concentrated solution (or suspension, etc.) of the additive to the gel solution before curing the gel. An additive also can be added to a gel by placing a cured hydrated gel, lacking the additive, in contact with an additive solution, upon which additive molecules pass into the hydrated gel as a result of the concentration gradient from the solution to the interior of the gel mass.

Although the hydrated gel unit preferably contains nutrients dissolved therein, it is possible to dissolve the additive in a separate additive-containing unit in contact with the gel unit. For example, the hydrated-gel mass lacking the additive is placed in contact with a second mass of the same or a different type of hydrated gel containing the additive. As a result of a concentration gradient of the additive between the two hydrated gel masses, the additive will migrate from the additive-containing gel mass to the gel mass originally lacking the additive.

Yet another way to provide a hydrated gel with an additive is to place a gel mass lacking the additive in contact with a hydrated gel mass comprising the additive in microencapsulated form or the additive associated with any substantially non-phytotoxic substance that will allow the additive dissolved or suspended therein to be bulk-transferred, e.g., via water convection, to the first gel mass. Representative substances include, but are not limited to, water, a second hydrated gel similar to the first hydrated gel, vermiculite, perlite, or any polymeric material that is non-phytotoxic and that can release the additive over time.

A number of appropriate nutrient formulations exist in the art, including a number of proprietary formulations. For example, a popular medium is the "MS liquid" (Murashige and Skoog, *Physiologia Plantarum* 15:473–497 (1962)) containing the following dissolved in water:

| | |
|---|---|
| $NH_4NO_3$ | 1650 mg/L |
| $KNO_3$ | 1900 mg/L |
| $CaCl_2.2H_2O$ | 440 mg/L |
| $MgSO_4.7H_2O$ | 370 mg/L |
| $KH_2PO_4$ | 170 mg/L |
| $Na_2EDTA$ | 37.25 mg/L |
| $FeSO_4.7H_2O$ | 27.85 mg/L |
| $MnSO_4.4H_2O$ | 22.3 mg/L |
| $ZnSO_4.4H_2O$ | 8.6 mg/L |
| $H_3BO_3$ | 6.2 mg/L |
| KI | 0.83 mg/L |
| $Na_2MoO_4.2H_2O$ | 0.25 mg/L |
| $CuSO_4.5H_2O$ | 0.025 mg/L |
| $CoCl_2.6H_2O$ | 0.025 mg/L |
| Glycine | 0.2 mg/100 $cm^3$ |
| Nicotinic Acid | 0.05 mg/100 $cm^3$ |
| Pyridoxine.HCl | 0.05 mg/100 $cm^3$ |
| Thiamine.HCl | 0.01 mg/100 $cm^3$ |
| Kinetin | 0.1 mg/L |
| Myo-inositol | 100 mg/L |
| IAA | 10 mg/L |
| Sucrose | 30000 mg/L |
| pH | 5.7–5.8 |

(Note: "MS medium" also contains 1.0% w/v agar, Murashige and Skoog, id.) When adding a nutrient solution to a gel solution, the concentrations of both solutions should be high enough such that the resulting mixture of the two solutions has the proper concentrations of gel solute and nutrients.

The nutrient solution can also include plant growth hormones and other compounds serving to further increase the probability of germinant survival.

As used herein, a "nutrient liquid" is an aqueous solution of nutrients similar to the "MS liquid" formulation. A "nutrient agar" is similar to the "MS medium." Changes in types and amounts of certain ingredients can be made to meet the needs of specific types of plants without departing in any substantial manner from the purpose and utility of a nutrient liquid or nutrient medium.

Since nutrient media, nutrient liquids, and any nutrient-containing hydrated gel is a rich growth medium for microorganisms and fungi, and other possible plant pathogens, it is important that all such liquids, as well as other additives and the totipotent plant tissue itself, be sterile before use. Totipotent plant tissue is kept sterile by culturing under sterile conditions. Liquids can be sterilized by any conventional means, e.g., autoclaving or microfiltration.

Oxygenated Hydrated Gels

To ensure that the totipotent plant tissue is provided with sufficient oxygen to undergo germination, a hydrated gel can be "oxygenated" to have a higher oxygen concentration than would otherwise be absorbed from the atmosphere. For example, the a non-phytotoxic oxygen-carrying or oxygen-absorbing substance can be added to the gel, or the gel can be oxygenated by other means, including subjecting the gel to a high-oxygen atmosphere under greater than atmospheric pressure.

Oxygenation of a gel can be achieved by any of several representative methods, as disclosed extensively in, for example, U.S. Pat. Nos. 5,236,469 and 5,427,593 (both incorporated herein by reference).

The minimum oxygen concentration required for germination of a manufactured seed is preferably at least adequate to support sufficient growth and germination of the radicle (structure that eventually becomes the plant root) of a particular plant species. The minimum oxygen concentration can be determined by a simple germination experiment involving a series of otherwise identical manufactured seeds each of which having a stepwise different oxygen concentration from all other manufactured seeds in the series.

Candidate oxygen carriers can be selected from the group consisting of perfluorocarbons (PFCs) and silicone oils. Representative perfluorocarbons include perfluorocycloalkanes, perfluoro(alkylcycloalkanes), perfluoro(alkylsaturated heterocyclics), and perfluoro(tert-amines). Use of these compounds in hydrated gels is disclosed extensively in U.S. Pat. Nos. 5,236,469 and 5,427,593 (both incorporated herein by reference). PFCs and silicon oils are preferably present in the hydrated gel as an emulsion that is preferably stabilized by substantially non-phytotoxic surfactant. Representative surfactants include methyl oxirane polymers, egg albumin, and other substantially non-phytotoxic surfactants such as those for food or ingestible pharmaceutical use. Generally, the concentration of the perfluorocarbon in the hydrated gel is about 15% w/v or less, and the concentration of silicone oil is about 30% w/v or less, depending on the surfactant, microdroplet size in the emulsion, etc. Generally, the concentration of surfactant is about 10% w/v or less.

Shoot Restraint

A manufactured seed according to the present invention preferably is configured so as to prevent entrapment of the shoot (and/or of structures situated at the rear of the shoot) within the manufactured seed, particularly in the artificial gametophyte.

Preferred restraints include, but are not limited to, any of various tube-like structures surrounding and is contacting the totipotent plant tissue, particularly all or part of the shoot end. The restraint, in turn, is disposed within the manufactured seed, e.g., in a cavity formed in the hydrated gel. The restraint permits transfer of water, nutrients, and oxygen from the gel to the totipotent plant tissue and, to such end, is preferably porous. The shoot end of the totipotent plant tissue is oriented toward a closed end of the tube and the radicle is oriented toward an open end. As the shoot elongates during germination, it impinges upon the closed end of the tube, which prevents entrapment of the shoot and urges the radicle to emerge from the open end of the porous tube.

Generally, appropriate shoot restraint can be achieved via a number of ways including, but not limited to, the following:

(1) Enclosing the totipotent plant tissue in a preformed cylinder that contacts, and preferably at least partially surrounds the plant tissue (particularly the shoot end). The cylinder is preferably encapsulated in a hydrated gel. The preformed cylinder is preferably porous and can be fabricated from suitable materials such as, but not limited to, glassy, metal, elastomeric, ceramic, clay, plaster, cement, starchy, putty-like, synthetic polymeric, natural polymeric, and adhesive materials.

(2) Forming a cavity in a hydrated gel "capsule" and attaching a porous material to the walls of the cavity before inserting a unit of totipotent plant tissue into the cavity. Candidate porous materials include, but are not limited to, dialysis tubing, natural sausage casing material, paper, fabric, and collagen materials.

(3) Forming a first cavity in a hydrated gel "capsule", filling the cavity with a conformable porous substance, then either forming a smaller-diameter second cavity in the porous substance coaxial with the first cavity before inserting a unit of totipotent plant tissue into the second cavity, or inserting the plant tissue directly into the porous substance in the first cavity. Alternatively, at least the shoot end of the plant tissue is dipped in the conformable porous substance before the plant tissue is inserted in the first cavity. Representative conformable porous materials include, but are not limited to, plaster of paris, cement, natural and synthetic polymers, tree resins, porous waxes, agar or alginate at a higher concentration than used for the gel capsule, and clays.

(4) "Hardening" the hydrated gel itself, before or after forming a cavity therein, that is, making the gel stiffer or more rigid by increasing the concentration of the gel solute, "surface drying," or by adding a particulate material to the gel (e.g., sand, plaster of paris, pulp fibers, cement, and polymeric substances.

(5) Inserting a sheet or piece of porous material between the plant tissue and the hydrated gel as the plant tissue is inserted into the gel. Candidate porous materials include, but are not limited to, paper, polymer-soaked paper, fabric, and polymer sheets.

(6) Forming a cavity in the hydrated gel, then applying a conformable porous coating on the walls of the cavity. Candidate coating materials include, but are not limited to, dry powdery materials such as plaster of paris or cement that, when wetted by liquid from the gel, form a porous barrier. Alternatively, a web-forming material can be applied to the walls of the cavity, such as gelatin powder, sponge material, natural webbing, and foams.

(7) Forming a gel capsule using a sufficiently concentrated gel solution to prevent a unit of totipotent plant tissue germinating therein from growing into and becoming entrapped in the gel.

Antibiotics, Plant Growth Regulators

A manufactured seed according to the present invention can also comprise one or more well known "antibiotics," i.e., agents known in the art that kill, prevent or inhibit the growth of, or repel pathogens, pests, and herbivores that are detrimental to the growth and development of the totipotent plant tissue including, but not limited to, bacteria, yeast, fungi, nematodes, insects, rodents, and birds. The antibiotic can be either a chemical compound or a beneficial organism that is effective in inhibiting the colonization of pathogens or that produces antibiotics. For example, a beneficial microbe (e.g., Mycostop™, Kemira Agro Oy, Helsinki, Finland) can be placed near the site of emergence of the primary root from the manufactured seed to colonize the root and preventing the root from becoming an area of entry for microbial pathogens in the soil. Microbes can also be added to enhance nutrient availability (e.g., nitrogen fixing bacteria or mycorrhizae) or otherwise to benefit the unit of totipotent plant tissue or the germinant developing therefrom. Antibiotics used in the practice of the present invention are compatible with growth and development of the totipotent plant tissue.

For example, a number of antibiotic compounds have been tested and found to be effective for use with totipotent plant tissue of Douglas-fir as additives to the hydrated gel. These include (together with recommended dosages) the antimicrobial compounds benzylpenicillin (100 mg/L), vancomycin (100 mg/L), ticarcillin (100 mg/L), cefamandole (10 mg/L), gentamicin (10 mg/L), and rifampicin (15 mg/L); the antifungal compounds miconazole (1 mg/L), amphotericin (2.5 mg/L); and "combination" antibiotic/antimycotic agents such as "A 7292" (Sigma Chemical Co., St. Louis, Mo., containing 10 mg/ml streptomycin, 6.06 mg/ml penicillin, and 25 µg/ml amphotericin B). Other dosages of these compounds and other antibiotics known in the art, particularly those employed for treating botanic seeds, can be employed as well, whether alone or in combination.

An antibiotic can be present in any part of the manufactured seed. For example, the antibiotic can be added directly to the synthetic gametophyte (hydrated gel) or be incorporated into or used to coat one or more layers of the seed coat. If the antibiotic is toxic to the totipotent plant tissue at high concentrations, the antibiotic can be restricted to the seed coat alone (or an outermost layer of a multi-layer seed coat), for example.

Various plant-growth regulators, alone or in combination can also be added to the artificial gametophyte or one or more seed coats of the manufactured seed. Representative plant-growth regulators include auxins, cytokinins, gibberellins (e.g., $GA_3$, $GA_{4/7}$, etc.), or other plant-growth regulators known in the art. It is preferred that such plant-growth regulators be present in the artificial gametophyte.

Long-Term Storage of Manufactured Seeds

The components of manufactured seed, particularly the totipotent plant tissue but also the artificial gametophyte, can germinate or decompose, respectively, if stored for extended periods under ambient conditions. However, depending on the composition of the various components of the manufactured seeds, manufactured seed can be prepared for long-term storage, for example, (1) by storing the manufactured seed (or at least the totipotent plant tissue) in an environment containing a respiration-limiting gas and/or reduced oxygen concentration, preferably at reduced temperatures; or, alternatively, (2) by freezing and/or dehydration of the assembled seed or one or more of the components of the seed before assembly. These storage methods can be combined with each other and with other methods known in the art for preventing the germination of totipotent plant tissue while maintaining its viability until time for sowing. See, for example, U.S. Pat. No. 5,666,762 (incorporated herein by reference).

For example, a manufactured seed can be prepared for long-term storage by the following process:

(1) Prepare a manufactured seed coat and partially fill the seed coat with a synthetic gametophyte, thereby producing a manufactured seed "capsule" (lacking a unit of totipotent plant tissue).

(2) Freeze the capsule, preferably to below about −3° C., more preferably to below about −10° C., by conventional freezing methods, e.g., using dry ice, liquid nitrogen, or an on-line freezer.

(3) Place a unit of totipotent plant tissue in a shoot constraint.

(4) Dehydrate the totipotent plant tissue and shoot restraint, preferably to a water content of less than about 10% or less. Conventional drying methods can be employed, e.g., use of a chemical desiccant such as $Ca(NO_3)_2$ to create a drying environment in which the totipotent plant tissue is kept until dry.

(5) Freeze the dehydrated totipotent plant tissue, preferably to below about −3° C., more preferably to below about −10° C. Conventional freezing methods can be used, preferably quick-freezing methods, e.g., using dry ice, liquid nitrogen, or an on-line freezer.

(6) Finish assembly of the manufactured seed at a temperature sufficiently low to avoid rehydration of the totipotent plant tissue, preferably below about −3° C., more preferably below about −10° C.

(7) Store the assembled seed at a temperature at or below the normal freezing temperature of the plant tissue (i.e., at a temperature below which ice crystals normally form in the plant tissue), preferably 0° C. or colder.

Structural Embodiments of Manufactured Seeds

Various possible embodiments of manufactured seeds within the scope of the present invention are disclosed in U.S. Pat. Nos. 5,236,469 and 5,701,699 (both incorporated herein by reference).

After preparing the gel liquid, preparing units of cured hydrated gel for use in making manufactured seeds can be done in a number of ways. Fluid transfer between the totipotent plant tissue and the hydrated gel can be accomplished, e.g., by direct contact or via an intervening water-permeable "bridge" such as filter paper. Preferably, the totipotent plant tissue is disposed in a preformed hole or cavity in a block of hydrated gel. The gel can be cured preformed into a preferred shape or can be formed as a larger cured mass and cut to size and shaped as desired before inserting the totipotent plant tissue.

Figure 1B:
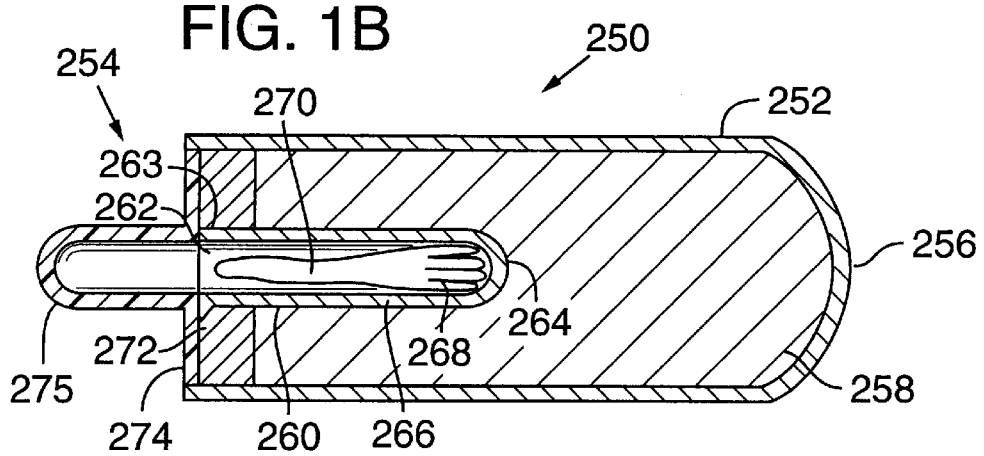
FIG. 1B is a sectional view of a preferred embodiment of a manufactured seed with a lid that includes a nipple.

Preferred embodiments of a manufactured seed according to the present invention are shown in FIG. 1A (flat lid) and FIG. 1B (lid with nipple). The manufactured seed 250 comprises a seed coat 252 substantially surrounding a hydrated gel 258 that serves as an artificial gametophyte for the unit of totipotent plant tissue 266. The seed coat 252 provides physical protection for the interior of the manufactured seed 250 while allowing the germinant that develops from the plant tissue 266 to escape from the manufactured seed during germination.

The seed coat 252 has an open end 254 and a closed end 256. The seed coat 252 can be constructed, for example, of a thin plastic material or a cellulosic material such as a portion of a common paper soda straw about 6.5 mm in diameter and 10–20 mm long that has been made water resistant by such means as dipping in a suitable liquid hot wax such as melted paraffin. A seed coat 252 made of cellulose or other biodegradable material is preferred so that nursery beds will not be cluttered with spent seed coats from previous crops, although it is preferred that the seed coat remain intact at least until emergence of the primary root.

The closed end 256 can be created by the use of a suitable plug or barrier or preferably simply by crimping to form a somewhat dome-shaped or conical end. A seed coat 14 to 18 mm long length will hold about 0.8 ml of gel. A volume of gel from 0.5 to about 1.0 ml is usually very satisfactory.

The hydrated gel 258 can be any of the types of gels discussed hereinabove, optionally comprising nutrients and oxygen carriers. A preferred gel 258 is agar-based because agar will gel (i.e., "set" or "cure") spontaneously by lowering the temperature. The hydrated gel 258 should be somewhat firm to prevent seepage of liquid from the gel into the cavity 262 containing the plant tissue. Flooding of the cavity 262 can cause low percentage of normal germinants. An agar concentration of about 1.8 g/L has proved to be very satisfactory.

The size of the seed coat 252 can vary, depending upon the species of plant being propagated. The dimensions and gel capacities recited above are suitable for propagation of totipotent plant tissue of conifers and should not be considered limiting for this or other types of plants.

The plant tissue 266 is contained within an inner tube 260 to provide, at least in part, sufficient shoot restraint. The inner tube 260 has an open end 263 and a closed end 264. The plant tissue 266 is situated within the manufactured seed 250 so as to orient the shoot end or cotyledons 268 toward the closed end 264 and the latent radicle 270 toward the open end 263.

The tube 260 can be made of various materials that are not phytotoxic and that permit adequate access of the totipotent plant tissue 266 to moisture, gases, and nutrients necessary for germination. The materials are also preferably porous. Materials such as, but not limited to, filter paper, plaster of paris, ceramics, and reasonably rigid open-celled foams have all proved satisfactory. A tube made from filter paper or similar material can optionally contain small perforations. For somatic embryos of conifers, a tube length of 4 to 8 mm and an internal diameter of about 1.5 to 3 mm has proven very satisfactory.

The internal diameter of the tube 260 should be sufficient to allow a somewhat enlarged shoot end 268 of the totipotent plant tissue to be in intimate contact with the walls of the tube 260. The tube 260 allows access of nutrients, gases, and liquids necessary for germination to the plant tissue. As stated above, the hydrated gel 258 should be firm enough to prevent excess liquid from seeping from the gel 258 into the cavity 262 occupied by the plant tissue 266.

The seed coat 252 can be filled with the hydrated gel 258 by any of a number of means that will apparent to those of ordinary skill in the art. A preferred method, especially for automated processes, is by use of an automatic pipette or syringe pump. Each seed coat 252 is filled to within a few millimeters of the open end 254 and the gel 258 allowed to set by cooling (if, e.g., agar is used) or by ion exchange (if sodium alginate is used).

A coaxial internal cavity is formed in the hydrated gel 258 to accept the tube 260. The cavity can be molded in the gel as the gel cures or formed after the gel has cured. Forming the cavity after the gel cures can be performed in a number of ways. For example, a thin-walled cylindrical steel tube used as a punch has proved very suitable. The gel core left within the steel tube can be readily removed by application of vacuum. The cavity thus formed in the cured gel should have an internal diameter about equal to the outside diameter of the tube 260 so that intimate contact therebetween is maintained. The tube 260 can be inserted into the cavity by use of a mandrel.

After forming or inserting the tube 260 in the cavity, the plant tissue 266 can be inserted into the tube 260 shoot-end first.

Either before or after insertion of the plant tissue 266, the manufactured seed 250 can be oxygenated as described previously.

A primary end seal 272 is applied over the gel surface and around the protruding open end 263 of the tube 260 before insertion of the plant tissue in the gel. However, the primary end seal 272 should not cover the open end 263 of the tube 260. This result can be readily achieved by inserting an appropriate mandrel in the end of tube 260 while the primary end seal 272 is being formed. It should be noted that a primary end seal is not necessary and may be omitted.

Many materials are suitable for the primary end seal 272. Ordinary paraffin wax has proved very satisfactory. The primary end seal 272 is typically 2 to 4 mm thick but this is not in any way critical.

A secondary end seal, or lid, 274 is applied so as to cover the open end 263 of the primary end seal 272. As shown in FIG. 1A, the lid 274 can be flat (either pre-stretched or unstretched). However, as shown in FIG. 1B, the lid preferably includes a nipple 275 that extends outwardly from the manufactured seed.

The lid 274 is preferably very thin, most typically no more than about 1 mm thick. It can be made of the same material as the primary end seal 272. For example, one way to form the lid 274 is to heat the surface of the primary end seal 272 sufficiently to cause surface melting thereof and draw a small amount of the molten material to form a film across the open end 263. Preferably, however, the lid 274 is a gas-permeable, water-impermeable membrane such as pre-stretched Parafilm®, which can be sealed in place across the open end 263 by heat annealing or mechanical pressure. Stretching a material such as Parafilm™ to produce a lid 274 having a protruding portion, or nipple, 275 as shown will cause a thinning of the lid in the pre-stretched region relative to the unstretched portion of the lid. The protruding portion can have any shape or configuration and may be symmetrical or asymmetrical in shape.

As with the seed coat 252, an antibiotic can optionally be added to or inside the primary and secondary end seals.

The closed end 264 on the tube 260 has been found to be advantageous. The closed end 264 prevents the shoot end or cotyledons 268 growing inside the tube 260 from penetrating the tube and expanding into the gel 258. Expansion of the shoot end or cotyledons 268 into the gel 258 would result in entrapment in the gel, preventing the growing plant from escaping from the manufactured seed and/or causing germinant abnormalities. The growing shoot end is preferably only temporarily restrained within the tube 260. As it grows and elongates, the shoot end bears against the internal surfaces of the tube; this urges the shoot end out of the tube and, consequently, out of the hydrated gel, simulating the function of a natural seed.

The germination sequence of a gymnosperm embryo from the embodiment of a manufactured seed 250 is as follows. After sowing, the manufactured seed 250 rests on or beneath the surface of soil or analogous plant-growth medium. At the onset of germination, before the germinating embryo bursts from the manufactured seed, nutrients (if any), oxygen and other gases, and water in the gel ("artificial gametophyte") pass from the gel 258 to the embryo. After the growing radicle burst open or penetrated the lid 274, atmospheric oxygen can enter the cavity 262 to provide oxygen to the embryo 266.

After germination commences, the cotyledons also enlarge and elongate, whereupon they bear against the inside walls of the restraint, including the closed end thereof, further facilitating a "natural" germination, which prevents the cotyledons growing within from penetrating into the gel and becoming entrapped in the gel.

Upon further growth, germinant has a longer root that may lift the capsule off the soil surface. The cotyledons assume a natural "bird cage" appearance as they further elongate out of the restraint. Finally, the germinant becomes fully upright and sheds the capsule in a manner analogous to the natural shedding of the remains of a botanic seed by a healthy germinant therefrom. The root continues to grow downward into the soil and the cotyledons spread apart. The germinant has excellent prospects for developing into a healthy plant.

Definitions

The following terms as used herein are defined as follows:

"Somatic embryo" is a plant embryo that developed via the laboratory culturing of totipotent plant cells or by induced cleavage polyembryogeny.

"Zygotic embryo" is a plant embryo removed from a seed of the corresponding plant.

"Germinant" is a unit of totipotent plant tissue that has undergone sufficient growth and development to emerge from a seed coat, analogous to emergence from a natural botanic seed.

"Radicle end" is that part of a unit of totipotent plant tissue that develops into the primary root of plant.

"Shoot" or "shoot end" is that part of a unit of totipotent plant tissue that develops into the aerial portions of the plant and includes the cotyledon(s), epicotyl, and/or hypocotyl.

"Cotyledon" refers generally to the first, first pair, or first whorl (depending on the plant type) of leaf-like structures on a plant embryo that function primarily to make food compounds in the seed available to the developing totipotent plant tissue but in some cases act as food storage or photosynthetic structures.

"Hypocotyl" is that portion of a plant embryo or seedling located below the cotyledons but above the radicle.

"Epicotyl" is that portion of the plant developed after germination from the stem apex.

"Capsule" refers to a manufactured seed exclusive of the unit of totipotent plant tissue therein.

"Hypocotyl length" pertains to the length of the hypocotyl at the time the hypocotyl was measured.

"Hypocotyl germination" denotes the emergence of a shoot from the capsule, caused by elongation of the hypocotyl sufficiently to burst the capsule. This term does not take into consideration any length criteria or lack of hypocotyl malformations.

"Partial germinants" are scored as any event from emergence of any part of the plant tissue from a manufactured seed, from penetration or dislodging of a lid by the radicle up to, but not including, the "full germinant" stage, which includes complete emergence of a germinant from a manufactured seed and complete shedding of the seed coat and shoot restraint.

"Swollen hypocotyl" is an attribute of an abnormal germinant characterized by the hypocotyl or a portion thereof having a greater than normal diameter compared with hypocotyls on control bare "germinants" grown on the surface of a nutrient agar or similar nutrient medium.

"Twisted hypocotyl" is an attribute of an abnormal germinant characterized by the hypocotyl having grooves spiraling longitudinally up or down the length of the hypocotyl. This defect is usually found only in germinants exhibiting swollen hypocotyls.

"Swollen cotyledons" is an attribute of an abnormal germinant of a gymnosperm characterized by unusually large cotyledon(s) compared to cotyledons on control bare "germinants" grown on the surface of a nutrient agar or similar nutrient medium.

"Twisted cotyledon" is an attribute of an abnormal germinant of a gymnosperm characterized by the cotyledon(s) having a spiraled or twisted appearance.

"Radicle length" pertains to the length of the radicle at the time the radicle is measured.

"Radicle germination" denotes the emergence or protrusive growth of the primary root from the capsule, caused by elongation of the radicle sufficient to burst the capsule. This term does not take into consideration any length criteria.

"Growth through seed coat" occurs when a unit of totipotent plant tissue inside the manufactured seed coat undergoes elongation both of the radicle and the hypocotyl and bursts the seed coat at both ends. This is usually evidenced by the seed coat remaining for a period of time as a captive body around the hypocotyl.

"Normalcy" denotes the presence of all parts (radicle, hypocotyl, cotyledon(s), epicotyl) of a germinant at time of evaluation. In the case of gymnosperms, a normal radicle has length greater than 3 mm and no visibly discernable malformations compared to the appearance of control bare "germinants" grown on the surface of nutrient agar or similar nutrient medium.

The invention will be better understood by reference to the following Examples, which are intended to merely illustrate the best mode now known for practicing the invention. The scope of the invention is not to be considered limited thereto, however.

EXAMPLES

Example 1

Natural Seed Model for Manufactured Seed

A baseline for natural seed vigor specifications is needed to better interpret the performance of manufactured seed. We sought to develop a natural seed model so that any point(s) in the process of germination of a manufactured seed can be quantitatively assessed. Therefore, we have created a quantitative and photographic baseline of hydrated and stratified seed germination kinetics and vigor during the first 5–7 weeks of development.

Orchard seed of Douglas-fir were stratified for approximately 8 weeks prior to sowing, or simply hydrated for 24 hours. The design required 320 seed per treatment, so 400 seed per treatment were sown approximately 5 mm deep in a simulated nursery bed in a growth chamber that simulated air and seed zone soil temperatures in Mima, Wash., during a 42 day period. A grid was constructed to fit over the bed to allow seed position to be easily located. Areas around drip points were covered with a funnel, and these areas were not sown. Treatments were sown in alternate rows of stratified and hydrated-only treatments. Seeds were sown across a row (horizontally) at string cross points only and down a column (vertically) both at and in-between string cross points. Seeds were planted 25 positions deep in vertical columns in the bed.

Among the notable features of the germinating seed was a pronounced stretching and bulging of the nucellar cap of the seed prior to emergence of the radicle.

Example 2

Determining the Burst Strength of Natural Botanic Seed

In these experiments we determined the force or pressure required for a penetrometer to break through the nucellus of a natural seed of Douglas-fir to simulate the radical of an embryo growing through the nucellar cap, an early occurrence in seed germination. Such data is useful for estimating the optimal burst strength of a lid for a manufactured seed containing totipotent plant tissue of Douglas-fir.

Figure 2:
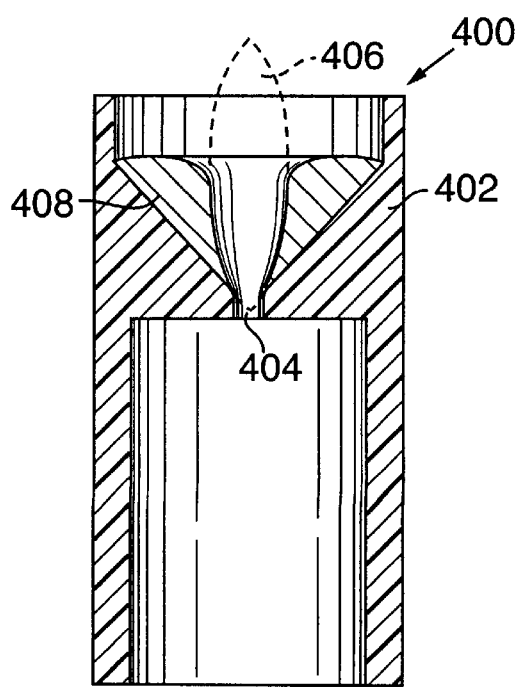
FIG. 2 is a cross-sectional view of a mold for penetrometer testing of the burst strength of a nucellar cap.

For our measurements we used a mold 400 that includes a generally cylindrical holder 402 with a central hole 404 that is smaller than the diameter of a typical Douglas-fir gametophyte but large enough to receive the end of a Douglas-fir gametophyte, as shown in cross-section in FIG. 2. An intact Douglas-fir gametophyte 406 was placed in the holder such that the radicle end was vertically aligned with the central hole 404 in the holder. Paraffin wax 408 was pipetted around the gametophyte 406 until the gametophyte was partially covered, and the wax 408 was allowed to harden. The gametophyte 406 was then removed, thus producing a wax mold of the gametophyte.

Figure 3:
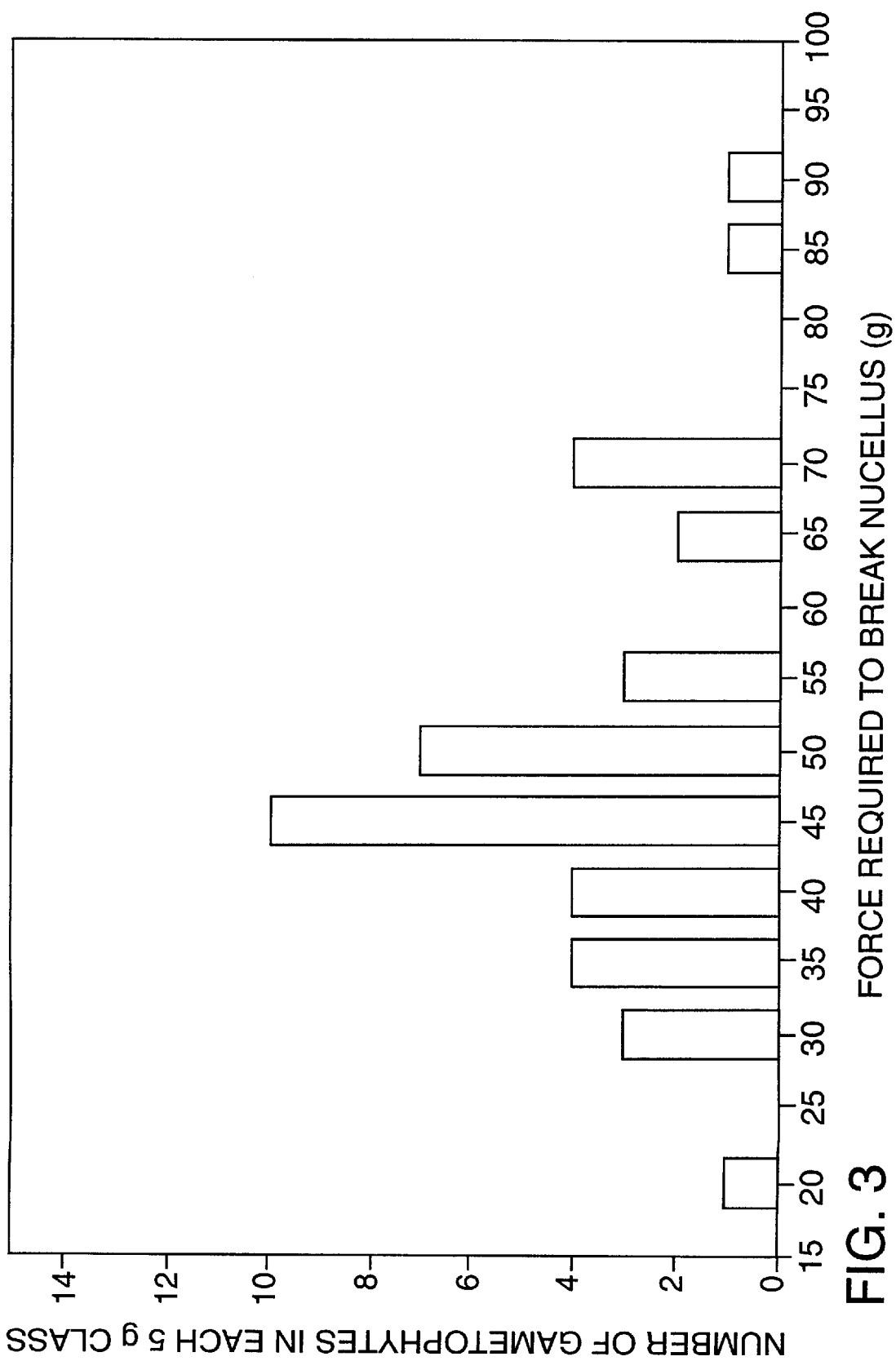
FIG. 3 is a graph showing the force (g) required to break the nucellus of Douglas-fir gametophytes.

To test the burst strength of the nucellar cap of a Douglas-fir gametophyte, the top half of a gametophyte (corresponding to the shoot end of the embryo) was cut away, the embryo removed from the corrosion cavity of the gametophyte, and the remaining gametophyte half (corresponding to the radicle end of the embryo) mounted in the mold 400 with the nucellar cap oriented downward and centered in the central hole 404. The mold was then placed on a scale or balance. A cylindrical penetrometer probe with a blunt, rounded tip was aligned with the hole in the holder was lowered into the corrosion cavity of the gametophyte half by means of a stepper motor. The highest value noted on the scale was recorded as the force required to break through the nucellar cap of the gametophyte half. The results are shown in FIG. 3.

Example 3
Comparison of Parafilm™ and Wax-Impregnated Kimwipe™ Lids

In these experiments we compared the germination rate for manufactured seed having various lid designs.

In earlier experiments, we produced lids by dipping circular pieces of a Kimwipe™ cellulosic tissue in melted paraffin wax, laying the dipped tissue circles on a Kimwipe™ tissue to drain away excess wax, and allowing the wax of the wax-impregnated Kimwipe™ lid to harden. We observed that a high proportion of such wax-impregnated Kimwipe™ lids either pop completely off or are lifted off by the hypocotyl, providing evidence that the forces generated by radical growth were not directed toward puncturing the Kimwipe™-based lid, but rather toward finding a way around the lid. Apparently, the radical cannot generate enough force to penetrate a Kimwipe™-based lid. Instead, upon contacting the lid, the radical turns and grows in a direction parallel to the lid. As a result, the lid "tents up" and the seal between the lid and the primary end seal (or cap) breaks.

This study was conducted to determine whether a Parafilm™ lid would allow the same level of germination and normalcy as a Kimwipe™-based lid. The Parafilm™ lids were pre-stretched to produce a nipple portion, then attached close to the opening in the primary end seal to cause the radical to grow into the nipple, thereby facilitating puncturing of the lid by the radical. The force of root growth would then be directed against the lid, as it is against the nucellar membrane in natural botanic seed. It was believed that this would simulate the events in early seed germination better than a flat, non-stretchable lid and promote germination similar to natural botanic seed.

Alternatively, it was considered possible that an attachment point towards the outer rim of the seed coat, far from the opening in the primary end seal, would facilitate more normal germination by allowing the radicle to exert forces on the lid directed toward popping off the lid, i.e., causing the lid to "tent up" and then break the bond between the primary and lids, as was observed with Kimwipe™-based lids (attachment close to the opening in the primary end seal is shown in FIG. 1B).

Manufactured seed were prepared as follows. Seed coats were created by cutting paper drinking straws into 22-mm sections. One section was slid onto a mandrel inserted into a electric drill, and one end of the straw was closed to seal by pushing the mandrel into a hole in a stainless steel block while the mandrel was turning. The resulting seed coat was approximately 18 mm long. Seed coats were then steam sterilized (121° C.). The paper in the seed coat was impregnated with wax by soaking the seed coats in a sterile molten wax bath containing paraffin and carnauba wax (9:1 by weight) with arasan (6% by weight; Thiram 50W Neutral, Gustafson, McKinney, Tex.) for approximately 30 sec. As the seed coats were removed, excess wax was drained and the coats were plunged into sterile cold water to quickly solidify the wax. The completed coats were then placed in a sterile dry Petri dish to dry in a laminar-flow hood until needed. A second, outer wax coat was provided by dipping the paper straw with the first wax coat, seal end down, into the molten wax-arasan mixture to coat the outside of the seed coat, then solidifying and drying the second coat as described.

The shoot restraints were made from Seeleys Pearl White Porcelain slips (Seeleys, Oneonta, N.Y.).

Artificial gametophyte medium (containing a perfluorocarbon emulsion and containing an elevated concentration of molecular oxygen compared to such medium lacking the emulsion) was prepared as described in U.S. Pat. No. 5,427,593 (incorporated herein by reference). The artificial gametophyte also contained 1 ml/L Sigma A 7292 (Sigma Chemical Co., St. Louis, Mo., combining 10 mg/mL streptomycin, 6.06 mg/mL penicillin, 25 µg/mL amphotericin B, hereinafter, "antimicrobial cocktail") and 0.1 mg/L $GA_{4/7}$ (a mixture containing, as tested, approximately equal parts of $GA_4$ and $GA_7$, Abbott Laboratories, North Chicago, Ill.). Hormone and antimicrobial additives were added directly to artificial gametophyte medium after autoclaving. Afterward, the medium was maintained at 44° C. to 50° C., a temperature is lower than normal (55° C.) due to the heat lability of the hormones and antibiotics used.

For attachment of lids close to the opening in the primary end seal, the lids were attached to the wax primary end seal by heat bonding, specifically by pressing down against the lid with the flat surface of a scalpel blade that had been heated to approximately 75° C. All the lid material not located directly over the opening in the primary end seal was attached to the primary end seal in these treatments. Lids that were attached far from the opening in the primary end seal were also attached by heat bonding. Wax-impregnated Kimwipe™-based lids were produced by cutting circles of Kimwipe™ tissues, dipping the circles in hot paraffin wax, draining away excess wax by placing the circles on dry Kimwipe™ tissues, and permitting the wax to harden. Lids were made by cutting circles of Parafilm™ with a #2 cork borer. Parafilm™ lids were sterilized by soaking in 50% Clorox™ bleach+two drops Tween-80™ per 500 mL for one-half hour, followed by four rinses with sterile water.

A straight (or standard) mold 420 for pre-stretching Parafilm™ lids is shown in FIGS. 4A–C. The mold 420 is generally cylindrical in shape and includes a top end 422 and bottom end 424. A cylindrical hole 426 for probe penetration extends along the central axis of the mold at least part way from the top end 422 toward the bottom end 424. A groove 428 for an O-ring 452 is provided in the top end 422 of the mold. A bevelled mold 440 for pre-stretching Parafilm™ lids is shown in FIG. 4D. The bevelled mold is similar to the straight mold of FIG. 4A except that a 45° bevel 442 is present at the top end of the central hole 426. The central hole 426 has a diameter slightly larger than the diameter of the penetrometer probe used with the mold. Different molds were used with Teflon™-coated penetrometer probes of different diameters.

The following terminology is used: a "straight" lid is produced using a straight mold and a "bevelled" lid using a bevelled mold. A "standard lid" is made using a "standard" sized "straight" mold and is "unfilled".

The use of the mold 420 to pre-stretch a Parafilm™ lid is shown in FIGS. 5A–B. The mold 420 is placed on a scale or balance. A Parafilm™ circle 450 was placed on the top end 422 of the mold. O-ring 452 was lowered into the groove 428 to hold the Parafilm™ circle 450 in place. A penetrometer probe 454 was then pressed downward into the hole 426, thereby stretching the Parafilm™ circle 450 and creating a lid 274 with a flat upper portion 276 and a "nipple" 275 (with a dome-, nipple-, or finger-like appearance, depending upon the depth of penetration of the probe) (FIGS. 5C and 5D). The interior of the nipple 278 has a cross-sectional diameter that can be about the same as or slightly larger than the diameter of the probe 454, although the interior diameter and depth of the nipple can decrease somewhat due to relaxation or partial collapse of the stretched Parafilm™ or collapsing of the nipples. The upper portion 276 of the lid can be trimmed to size, if desired.

For "standard" lids, a 0.062-in diameter (1.57 mm) penetrometer probe was employed, with a depth of penetration of approximately 0.107 in (2.72 mm) (average of three replicates). For the "larger" lids, a 0.080-in diameter (2.03 mm) penetrometer probe was used, with the depth of penetration being approximately 0.140 in (3.56 mm).

To produce a "filled" lid, 2–3 µL agar medium including a PFC was introduced into the nipple produced by pre-stretching a Parafilm™ lid and allowed to harden.

Figure 6:
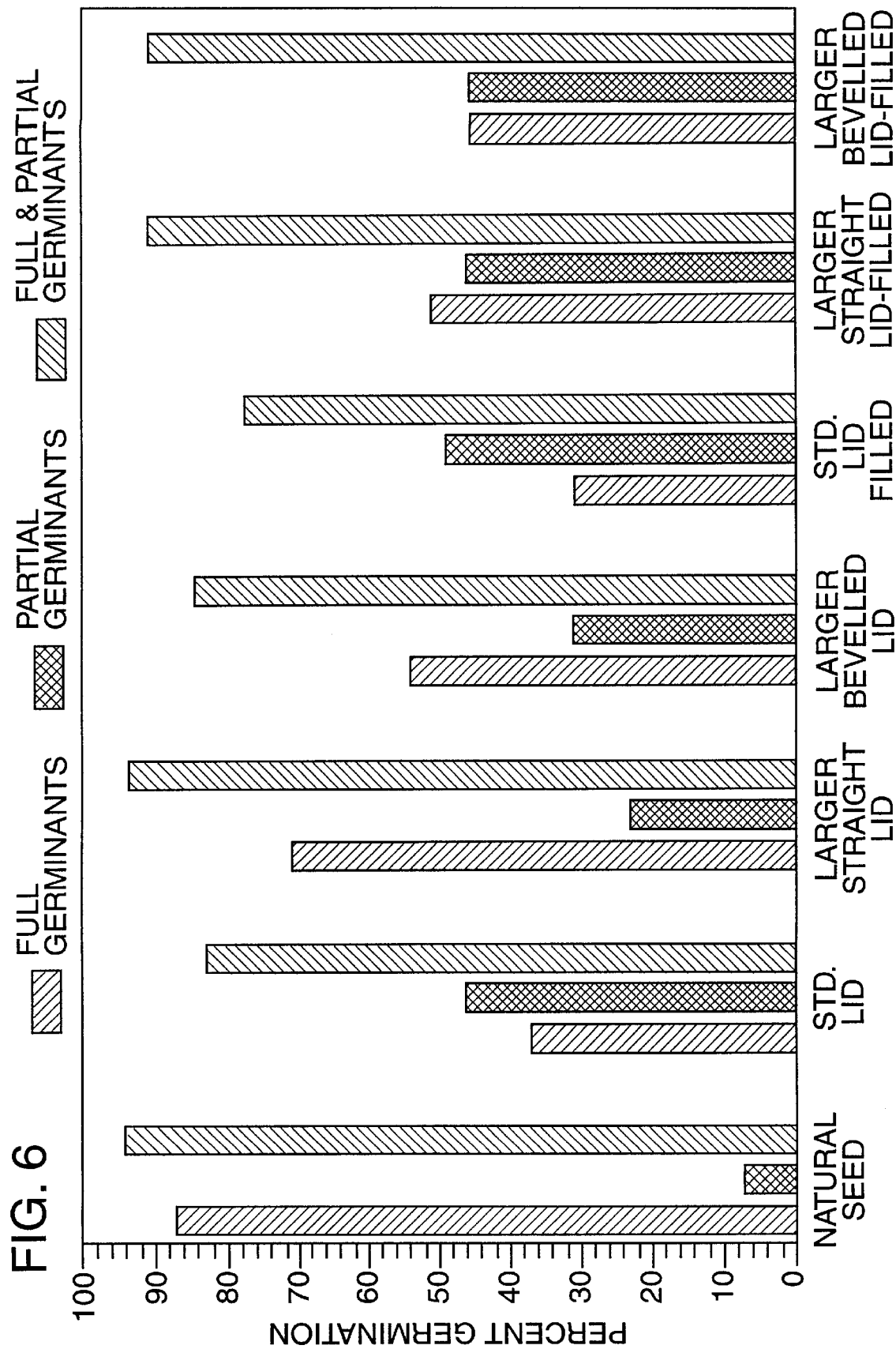
FIG. 6 is a bar graph showing the percent germination of manufactured seed having various lid designs.

As shown in FIG. 6, the percentage of full germinants was higher for manufactured seed having lids that were made using the 0.080-in probe ("larger straight lid" in FIG. 6) than the 0.062-in probe ("standard straight lid" in FIG. 6).

Example 4

Effect of Point of Attachment of Lids on Germination Frequency of Manufactured Seed Containing Douqlas-Fir Zygotic Embryos Manufactured seed were prepared as described above (Example 3). All manufactured seed were sown in sterile sand and incubated in the lab at room temperature for four weeks.

We tested manufactured seed having the following six treatments:

(1) No lid.
(2) Kimwipe™-based lid.
(3) Parafilm™ lid (not pre-stretched) attached near the outer edge of the top surface of the primary end seal (farthest from the opening in the primary end seal).
(4) Parafilm™ lid (not pre-stretched) attached to the top surface of the primary end seal close to the opening therein.
(5) Pre-stretched Parafilm™ lid attached near the outer edge of the top surface of the primary end seal.
(6) Pre-stretched Parafilm™ lid attached to the top surface of the primary end seal close to the opening therein.

The experimental design was based on a randomized complete block. Thirty seed were tested for each treatment, with five seed per treatment per block. One extra repetition was sown in non-sterile soil and placed in a growth chamber. The dependent variables were normal germination and radical and hypocotyl lengths. The germination tray was a blocking factor.

The results are shown in Tables 1–3. In the arcsine-transformed data, treatments 1 and 2 produced significantly more normal germinants than all other treatments in this study ($\rho=0.0001$. This difference was also observed in the non-transformed data.

No significant differences were detected in radical length, but differences in hypocotyl length were found between treatments. Treatment 4 produced significantly shorter hypocotyls than all treatments except Treatment 3.

Differences were not detected in primary end seal thickness at $\alpha=0.05$, but at $\alpha=0.06$ such differences would have been detected. Blocks 1 and 2 appear to have slightly thinner primary end seals than the other blocks, but this difference was not significant between all blocks.

It is apparent that a Kimwipe™-based lid, which is easily dislodged, is beneficial compared to normal germination in sterile sand. However, a Kimwipe™-based lid has not performed well in small tests in non-sterile soil, perhaps because the seal around the opening in the primary end seal is insufficient to prevent microbial contamination.

The unstretched Parafilm™ lid failed to allow the same level of germination as the Kimwipe™-based lid, possibly of the different sealing methods used. Kimwipe™-based lids were attached without heat by pressing the lid against the primary end seal. They readily stuck to the wax primary end seal. Parafilme lids were attached with heat. The heat seal may have been more difficult to break than the cold seal, resulting in fewer normal germinants.

TABLE 1

Effect of Treatment on Normalcy and Germination (%)

| | Treatment | | | | | |
|---|---|---|---|---|---|---|
| | 1 | 2 | 3 | 4 | 5 | 6 |
| Normalcy (%) | 76.67 | 63.33 | 16.67 | 3.33 | 20.00 | 30.00 |
| Full germ. (%) | 83.33 | 63.33 | 16.67 | 6.67 | 20.00 | 30.00 |
| Partial germ. (%) | 10.00 | 13.33 | 36.67 | 20.00 | 53.33 | 40.00 |
| No germ. (%) | 3.33 | 23.33 | 36.67 | 73.33 | 20.00 | 23.33 |

TABLE 2

Effect of Treatment on Percent of Germinants with Radical and Hypocotyl Growth Outside the Manufactured Seed

| | Treatment | | | | | |
|---|---|---|---|---|---|---|
| | 1 | 2 | 3 | 4 | 5 | 6 |
| Radical growth | 93.33 | 96.67 | 66.67 | 63.33 | 76.67 | 90.00 |
| Hypocotyl growth | 96.67 | 96.67 | 60.00 | 50.00 | 86.67 | 93.33 |

TABLE 3

Effect of Treatment on Percent of Embryos that Opened Lid and Manner of Opening of Lid by Embryo

| | Treatment | | | | | |
|---|---|---|---|---|---|---|
| | 1 | 2 | 3 | 4 | 5 | 6 |
| Grew through lid | N/A | 3.33 | 13.33 | 26.67 | 83.33 | 93.33 |
| Pried off lid | N/A | 66.67 | 50.00 | 33.33 | 3.33 | 0.00 |
| Lid did not open | N/A | 30.00 | 33.33 | 40.00 | 13.33 | 6.67 |

Pre-stretched Parafilm™ lids performed better than unstretched Parafilm™ lids, with higher radical and hypocotyl growth, germination, and normalcy. The number of embryos that grew through the lid was much higher in the pre-stretched lid treatments than in any other treatments. These results support our hypothesis regarding the mechanism for radical penetration and indicate that the channeling of the root into the nipple resulting from pre-stretching facilitates penetration of the lid. Even though the germination and normalcy rates were low in the pre-stretched lid treatments, the number of germinants that penetrated the lid (similar to penetration of the nucellus of a natural botanic seed) was high.

It also appears that attachment of the lids close to the opening in the primary end seal was beneficial for pre-stretched lids but did not matter for unstretched lids. Although normal germination was similar for both attachment points with pre-stretched lids, radical growth was about 14% greater and hypocotyl growth about 7% greater when the pre-stretched lids were attached close to the opening in the primary end seal.

Pre-stretched lids promoted more normal germination. Root and hypocotyl growth and emergence from seed with pre-stretched lids was as high as manufactured seed that lacked lids or that had wax-impregnated Kimwipe™ lids.

With pre-stretched lids, embryos germinated in a fashion similar to natural seed- When the radicle of the germinant punctures the lid, a seal is created around the radicle extending outside the manufactured seed coat, which may prevent microbes from entering the seed and competing with the embryo for nutrients.

Example 5

Effect of Nipple Size on Germination and Normalcy of Manufactured Seed Containing Douglas-Fir and Loblolly Pine Zygotic Embryos In these experiments, pre-stretched Parafilm™ lids were created with probes of different diameters to test the effect of the size of the nipple on germination and normalcy of germinants from manufactured seed containing Douglas-fir or loblolly pine zygotic embryos.

Manufactured seed were prepared essentially as described above (Example 3). Lids were made using strips of Parafilm™ M laboratory film (American National Can, Greenwich, Conn.) that were cut to 4 in ×⅝ in (101.6 mm ×15.88 mm) that were pre-stretched using penetrometer probes having diameters of 0.06 in (1.52 mm), 0.08 in (2.03 mm), 0.10 in (2.54 mm), 0.115 in (2.92 mm), and 0.132 in (3.35 mm). The mold was placed on a balance and, for each probe, the penetrometer stopper point was selected as the point at which the balance read about 190 grams. It was observed that the larger the probe diameter, the farther the Parafilm™ could be stretched. The probe was raised five seconds after being lowered to the stopper point. After pre-stretching, the lids were cut from the strip using a 6 mm Acu-punch™ (Accuderm, Inc., Fort Lauderdale, Fla.). Lids were attached close to the opening in the primary end seal (see Example 4). Non-stretched (flat) Parafilm™ lids were included for the sake of comparison.

All manufactured seed were sown in sterile sand and incubated in the lab at room temperature.

Figure 7:
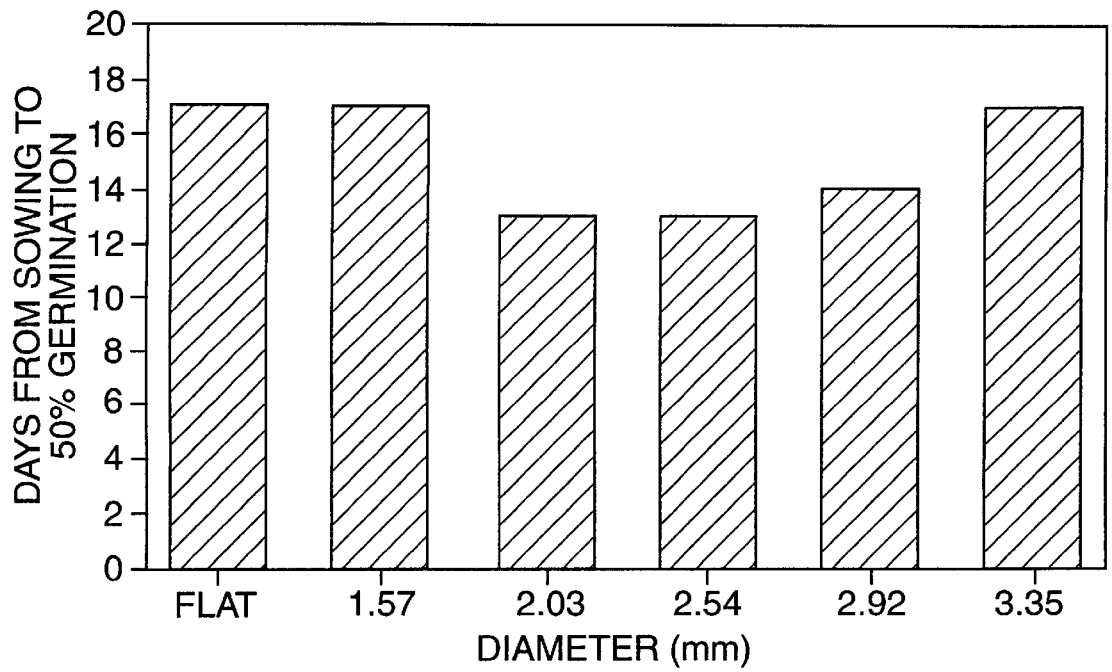
FIG. 7 is a bar graph showing the effect of the diameter (mm) of pre-stretched Parafilm™ lids on the germination (days from sowing to 50% germination) of manufactured seed that are made with Douglas-fir zygotic embryos.
Figure 8:
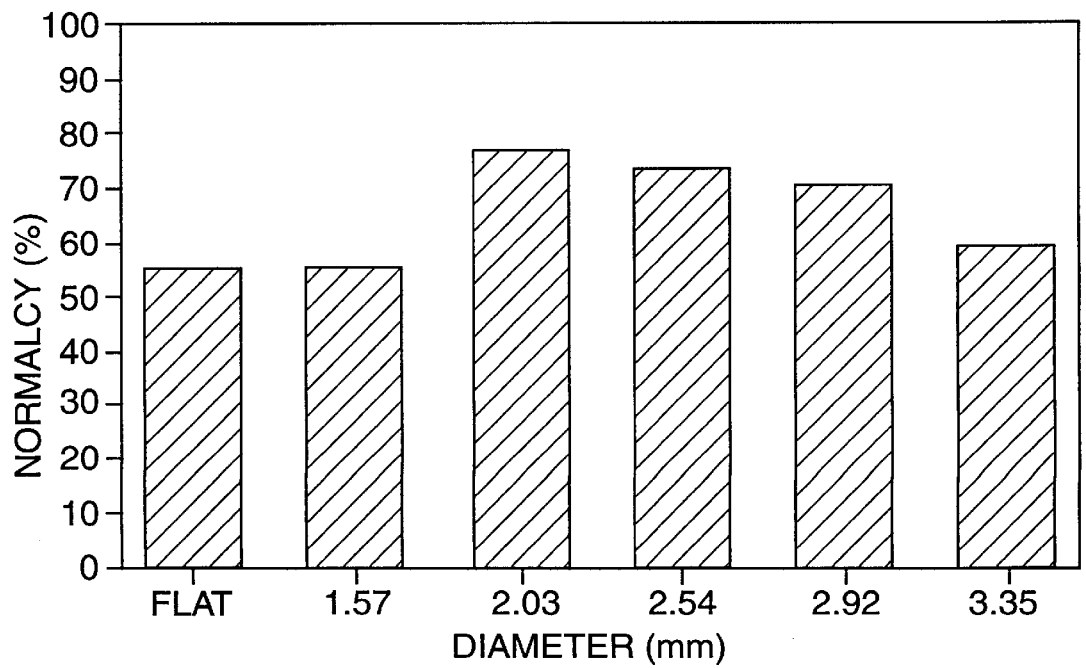
FIG. 8 is a bar graph showing the effect of the diameter (mm) of pre-stretched Parafilm™ lids on germinant normalcy (% normal germinants at 38 days after sowing) for manufactured seed that are made with Douglas-fir zygotic embryos.
Figure 9:
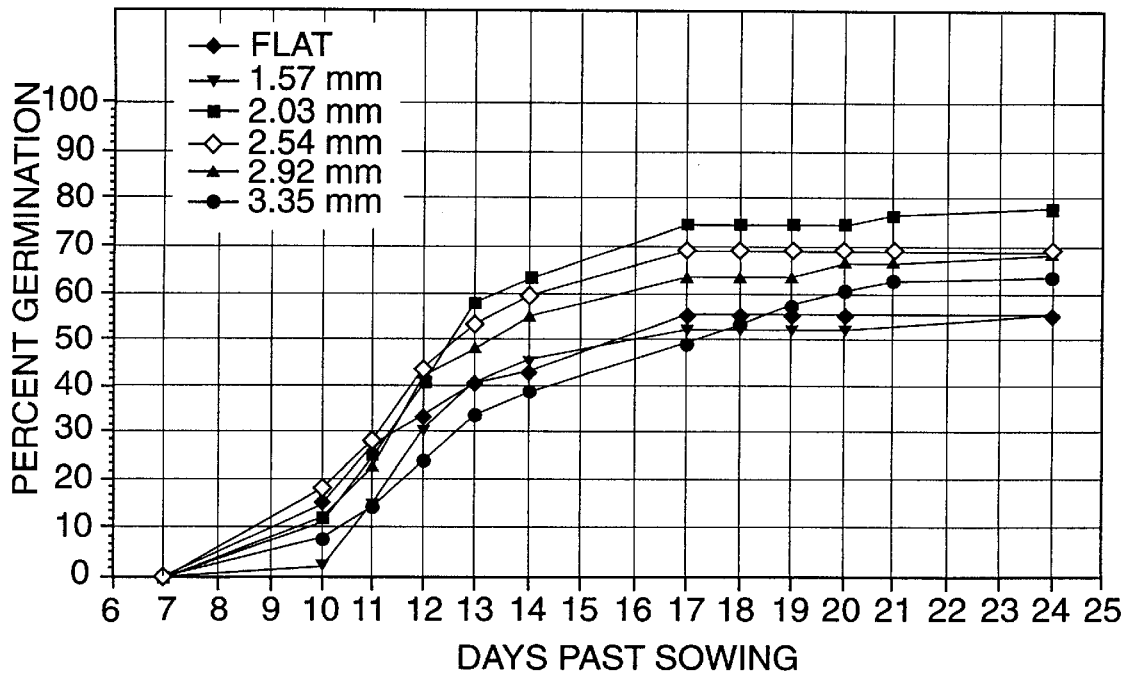
FIG. 9 is a graph showing the effect of the diameter (mm) of pre-stretched Parafilm™ lids on percent germination (full germinants) from 7 to 24 days after sowing for manufactured seed that are made with Douglas-fir zygotic embryos.
Figure 10:
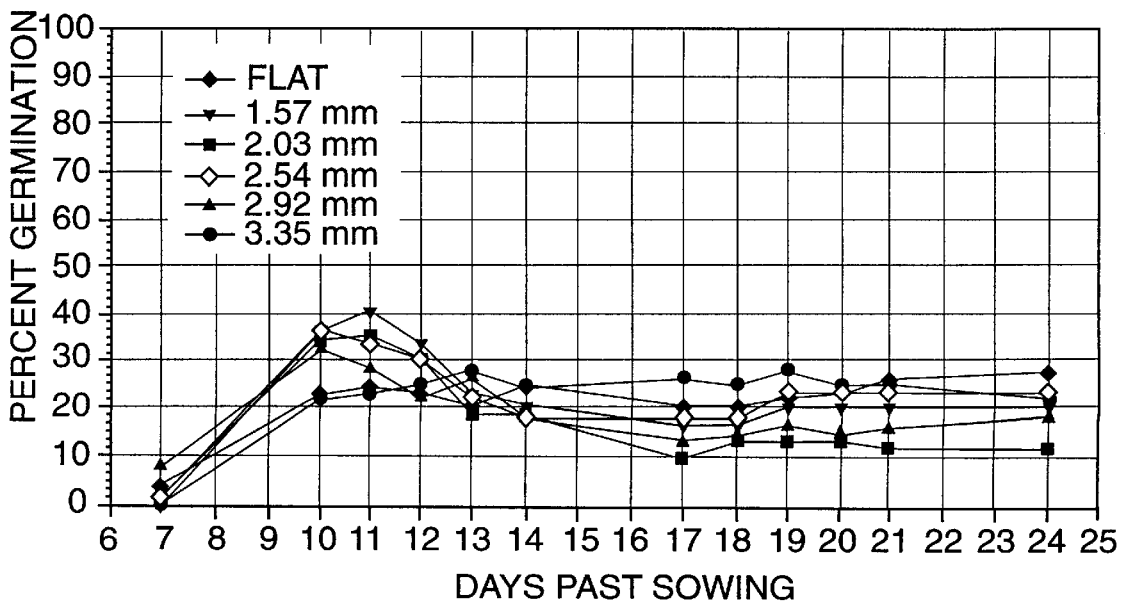
FIG. 10 is a graph showing the effect of the diameter (mm) of pre-stretched Parafilm™ lids on percent germination (partial germinants) from 7 to 24 days after sowing for manufactured seed that are made with Douglas-fir zygotic embryos.

The diameter of pre-stretched lids had a significant impact on germination rate and normalcy. For Douglas-fir, on average, pre-stretched lids were better than flat lids. Lids pre-stretched with 0.08 in and 0.10 in probes produced the best results in terms of germination rate (days to 50% germination, a standard measure of germination vigor) and normalcy at 38 days after sowing (Table 4; FIGS. 7 and 8). Lids pre-stretched with 0.08-in, 0.10-in, and 0.115-in probes produced the best results in terms of total germination and speed of germination (FIGS. 9 and 10). However, lids pre-stretched with 0.062-in and 0.132-in probes did not differ significantly in performance from flat lids.

TABLE 4

Effect of Treatment on Normalcy and Speed of Germination

| Treatment | Normalcy (%) | Days to 50% Germination |
| --- | --- | --- |
| Flat | 56.7$^C$ | 17 |
| 0.06" | 56.7$^C$ | 17 |
| 0.08" | 78.3$^A$ | 13 |
| 0.10" | 74.6$^{A,B}$ | 13 |
| 0.115" | 71.7$^{A,B,C}$ | 14 |
| 0.132" | 60.0$^{B,C}$ | 17 |

Note to Table 4: Different letter in superscript denotes significant difference ($\alpha = 0.05$).

Figure 11:
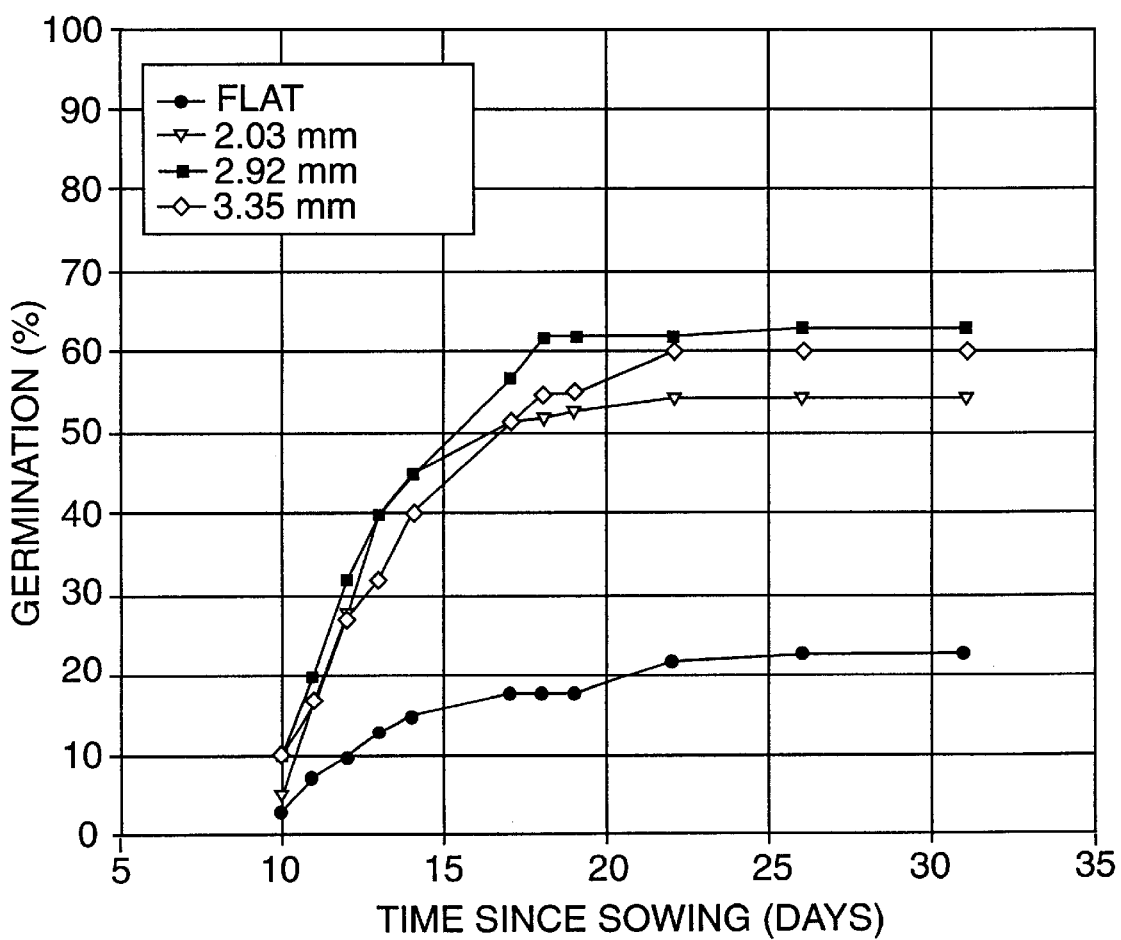
FIG. 11 is a graph showing the effect of the diameter (mm) of pre-stretched Parafilm™ lids on percent germination from 10–31 days after sowing for manufactured seed including loblolly pine zygotic embryos.

The results were even more dramatic with manufactured seed that included loblolly pine zygotic embryos. For loblolly pine, 0.08-in and 0.10-in probes produced lids that resulted in earlier germination (FIG. 11) and higher normalcy (Table 5).

It is possible that if the diameter of the nipple is too large, the radicle can curve back on itself instead of penetrating the lid, reducing the efficacy of the nipple.

TABLE 5

Effect of Nipple Diameter on Normalcy of Loblolly Pine Germinants

| Probe Diameter | % Normalcy* |
| --- | --- |
| Flat | 25.0 |
| .08" | 55.0 |
| .10" | 61.7 |
| .115" | 60.4 |

Note to Table 5: Normalcy figure for each of the pre-stretched lids was different to a statistically significant degree from the flat lid, but not to other pre-stretched lids.

In other experiments, it was demonstrated that water loss from manufactured seed was very slow with both unstretched and pre-stretched Parafilm™ lids at low (20%) relative humidity.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

What is claimed is:

1. A manufactured seed comprising:
   a totipotent plant tissue, and
   a manufactured seed coat containing the totipotent plant tissue that comprises an orifice and a lid that covers the orifice, the lid produced by pre-stretching a wax or polymer film with a probe, the lid comprising a protruding portion.

2. The manufactured seed of claim 1 wherein the lid is penetrable by the totipotent plant tissue upon germination.

3. The manufactured seed of claim 1 wherein at least the protruding portion of the lid is penetrable by the totipotent plant tissue upon germination.

4. The manufactured seed of claim 1 wherein the lid comprises Parafilm™.

5. The manufactured seed of claim 1 wherein the probe has a diameter between about 1.52 mm and about 3.35 mm.

6. The manufactured seed of claim 1 wherein the manufactured seed coat is water-impermeable until the totipotent plant tissue penetrates or dislodges the lid.

7. The manufactured seed of claim 6 wherein the lid is water-impermeable and gas-permeable.

8. The manufactured seed of claim 1 wherein the totipotent plant tissue comprises a radicle and the radicle is oriented toward the protruding portion of the lid.

9. The manufactured seed of claim 1 further comprising a nonphytotoxic hydrated gel disposed within the manufactured seed coat so as to permit liquid transfer from the gel to the totipotent plant tissue.

10. The manufactured seed of claim 1 wherein the manufactured seed coat comprises a material selected from the group consisting of a cellulosic material, glass, plastic, a cured polymeric resin, paraffin, wax, varnish, and combinations thereof.

11. A manufactured seed comprising:

a totipotent plant tissue, and a manufactured seed coat containing the totipotent plant tissue that comprises an orifice and a lid that covers the orifice, the lid comprising a protruding portion, that includes a generally cylindrical portion having a cross-sectional diameter selected to provide significantly better germination than a flat lid of the same material.

12. The manufactured seed of claim 11 wherein the cross-sectional diameter is between about 1.52 mm and about 3.35 mm.

13. A manufactured seed comprising:

a totipotent plant tissue comprising a radicle, a manufactured seed coat enclosing the totipotent plant tissue that comprises an orifice and a lid that covers the orifice, the lid produced by pre-stretching a wax or polymer film with a probe, the lid comprising a protruding portion, and a nonphytotoxic hydrated gel disposed within the manufactured seed coat so as to permit liquid transfer from the gel to the totipotent plant tissue, wherein the radicle of the totipotent plant tissue is oriented toward the protruding portion of the lid.

14. The manufactured seed in claim 13, wherein the probe has a diameter between about 1.52 mm and about 3.35 mm.

15. A method of making a manufactured seed comprising:

providing a manufactured seed coat that comprises an orifice, inserting a totipotent plant tissue into the manufactured seed coat through the orifice, covering the orifice with a lid produced by pre-stretching a wax or polymer film, the lid comprising a protruding portion such that, upon germination of the totipotent plant tissue, the totipotent plant tissue preferentially enters and contacts the protruding portion and dislodges or penetrates the lid.

16. The method of claim 15, comprising the step of pre-stretching Parafilm™ with a probe to produce the lid.

17. The method of claim 16 comprising pre-stretching Parafilm™ with a probe having a diameter between about 1.52 mm and about 3.35 mm.

18. The method of claim 15 comprising inserting the totipotent plant tissue comprising a radicle into the manufactured seed coat such that the radicle is oriented toward the orifice.

19. The method of claim 15 comprising providing a manufactured seed coat comprising a nonphytotoxic hydrated gel, the method comprising disposing the totipotent plant tissue within the manufactured seed coat so as to permit liquid transfer from the gel to the totipotent plant tissue.

20. A method for germinating a totipotent plant tissue comprising:

(a) providing a manufactured seed according to claim 1; and (b) incubating the manufactured seed under conditions suitable for germination of the totipotent plant tissue.

21. A manufactured seed comprising:

a totipotent plant tissue comprising a radicle, and a manufactured seed coat containing the totipotent plant tissue that comprises an orifice and a lid that covers the orifice, the lid comprising a weakened portion the radicle of the totipotent plant tissue being oriented toward the orifice.

22. The manufactured seed of claim 21, wherein the lid comprises a wax or polymer film.

23. A manufactured seed comprising:

a totipotent plant tissue comprising a radicle;

a manufactured seed coat enclosing the totipotent plant tissue that comprises an orifice and a lid that covers the orifice, the lid comprising a weakened portion, and a non-phytotoxic hydrated gel disposed within the manufactured seed coat so as to permit liquid transfer from the gel to the totipotent plant tissue, wherein the radicle of the totipotent plant tissue is oriented toward the weakened portion of the lid.

24. The manufactured seed of claim 23, wherein the lid comprises a wax or polymer film.

25. A method of making a manufactured seed comprising:

providing a manufactured seed coat that comprises an orifice, inserting a totipotent plant tissue comprising a radicle into the manufactured seed coat through the orifice, the radicle of the totipotent plant tissue being toward the orifice, producing a lid for the orifice, the lid having a weakened portion, and covering the orifice with the lid such that, upon germination of the totipotent plant tissue, the totipotent plant tissue contacts the weakened portion and penetrates the lid.

26. The method of claim 25, wherein the lid is produced by weakening a portion of a wax or polymer film.

* * * * *